United States Patent [19]
Popoff et al.

[11] Patent Number: 5,824,795
[45] Date of Patent: Oct. 20, 1998

[54] OLIGONUCLEOTIDES FOR THE DETECTION OF SALMONELLA

[75] Inventors: Michel Y. Popoff, Plaisir; Muriel Le Guern Fellous, Rueil-Malmaison, both of France

[73] Assignees: Institut Pasteur; Institut National de la Sante et de la Recherche Medicale, both of Paris Cedex, France

[21] Appl. No.: 586,272

[22] Filed: Jan. 16, 1996

[30] Foreign Application Priority Data

Jan. 16, 1995 [FR] France ..................................... 9500410

[51] Int. Cl.$^6$ .......................... C07H 12/04; C07H 21/02; C12Q 1/68

[52] U.S. Cl. ................................ 536/24.3; 536/231; 435/6

[58] Field of Search ................. 435/6; 536/23.1, 536/24.3; 935/77, 78

[56] References Cited

U.S. PATENT DOCUMENTS 4,358,535  11/1982  Falkow et al. ............................... 435/5

FOREIGN PATENT DOCUMENTS

| WO9201056 | 1/1992 | WIPO . |
| WO 93/04202 | 3/1993 | WIPO . |
| WO 93/18165 | 9/1993 | WIPO . |
| WO 95/00664 | 1/1995 | WIPO . |

OTHER PUBLICATIONS

Matthews et al., Analytical Biochemistry 169:1–25 (1988).
Bajaj et al., Molecular Microbiology 18(4):715–727 (1995).
Steffan et al., Annual Review of Microbiology 45:137–161 (1991).

The Stratagene Catalog, p. 39 (1988).

Res. Microbiology, vol. 146, No. 1, pp. 17–20, Jan. 1995, I. Miras, et al., "Nucleotide Sequence of iagA and iagB Genes Involved in Invasion of HeLa Cells by Salmonella Enterica Subsp. Enterica Ser. Typhi".

Molecular and Cellular Probes, vol. 7, pp. 187–197, 1993, D. Chevrier, et al., "PCR Product Quantification by Non–Radioactive Hybridization Procedures Using An Oligonucleotide Covalently Bound to Microwells".

FEMS Immunology and Medical Microbiology, vol. 10, pp. 245–251, Feb. 1995, D. Chevrier, et al., "Rapid Detection of Salmonella Subspecies I by PCR Combined with Non–Radioactive Hybridisation Using Covalently Immobilised Oligonucleotide on a Microplate".

*Primary Examiner*—W. Gary Jones
*Assistant Examiner*—Ethan Whisenant
*Attorney, Agent, or Firm*—Oblon, Spivak, McClelland, Maier & Neustadt, P.C.

[57] ABSTRACT

The subject of the invention is new means, comprising nucleotide sequences, for the detection, especially after amplification, of the DNA or of the cDNA of *S. enterica* or *S. bongori*.

The invention relates especially to the oligo-nucleotides having the nucleotide sequence of SEQ ID NO:4–18.

9 Claims, 12 Drawing Sheets

```
1
GTA CTA GCA GCA GAA TTA CTG AAA CAG TAG ATT CTA TCC TAA CGA CTT GTA TTA GCT ATT
                               31                                  iagA
61
ATA ACT TTT CAC CCT GTA AGA GAA TAC ACT ATT ATC ATG CCA CAT TTT AAT CCT GTT CCT
                               91                   met pro his phe asn pro val pro
121                                                151
GTA TCG AAT AAA AAA TTC GTC TTT GAT GAT TTC ATA CTC AAC ATG GAC GGC TCC CTC GTA
val ser asn lys lys phe val phe asp asp phe ile leu asn met asp gly ser leu val
181                                                211
CGC TCA GAA AAG AAA GTC AAT ATT CCA AAA GAA TAT GCC GTT CTG GTC ATC CTC
arg ser glu lys lys val asn ile pro lys glu tyr ala val leu val ile leu leu
241                                          271
GAA GCC GGC AAG ATT GTG AGT AAA AAC ACC TTA TTG GAC CAA GTA TGG GGC GAC GCG
glu ala ala gly lys ile val ser lys asn thr leu leu asp gln val trp gly asp ala
301                                          331
GAA GTT AAC GAA GAA TCT CTT ACC CGC TGT ATC TAT GCC TTA CGA CGT ATT CTG TCG GAA
glu val asn glu glu ser leu thr arg cys ile tyr ala leu arg arg ile leu ser glu
361                                          391
GAT AAA GAG CAT CGT TAC ATT GAA ACA CTG TAC GGA CAG GGT TAT CGG TTT AAT CGT CCG
asp lys glu his arg tyr ile glu thr leu tyr gly gln gly tyr arg phe asn arg pro
421                                          451
GTC GTA GTG GTG TCT CCG CCA GCG CCG CAA CCT ACG ACT CAT ACA TTG GCG ATA CTT CCT
val val val val ser pro pro ala pro gln pro thr thr his thr leu ala ile leu pro
```

FIG. 1A

```
481
TTT CAG ATG CAG GAT CAG GTT CAA TCC GAG AGT CTG CAT TAC TCT ATC GTG AAG GGA TTA
phe gln met gln asp gln val gln ser glu ser leu his tyr ser ile val lys gly leu
                                  511                                  571
TCG CAG TAT GCG CCC TTT GGC CTG AGC GTG CTG CCG GTG ACC ATT ACG AAG AAC TGC CGC
ser gln tyr ala pro phe gly leu ser val leu pro val thr ile thr lys asn cys arg
                                                              631
AGT GTT AAG GAT ATT CTT GAG CTC ATG GAT CAA TTA CGC CCC GAT TAT TAT ATC TCC GGG
ser val lys asp ile leu glu leu met asp gln leu arg pro asp tyr tyr ile ser gly
                                              691
CAG ATG ATA CCC GAT GGT AAT GAT AAT ATT GTA CAG ATC GAG ATA GTT CGG GTT AAA GGT
gln met ile pro asp gly asn asp asn ile val gln ile glu ile val arg val lys gly
                      721                                                  751
TAT CAC CTG CTG CAC CAG GAA AGC ATT AAG TTG ATA GAA CAC CAA CCC GCT TCT CTC TTG
tyr his leu leu his gln glu ser ile lys leu ile glu his gln pro ala ser leu leu
          781                                                      811
CAA AAC AAA ATT GCG AAT CTT TTG CTC AGA TGT ATT CCC GGA CTT CGC TGG GAC ACA AAG
gln asn lys ile ala asn leu leu leu arg cys ile pro gly leu arg trp asp thr lys
                          841                                              871
CAA ATT AGC GAG CTA AAT TCG ATT GAC AGT GAC ATG GTC TAC TTA CGC GGT AAG CAT GAG
gln ile ser glu leu asn ser ile asp ser asp met val tyr leu arg gly lys his glu
                                  901                                              931
TTA AAT CAA TAC ACC CCC TAT AGC TTA CAG CAA GCG CTT AAA TTG CTG ACT CAA TGC GTT
leu asn gln tyr thr pro tyr ser leu gln gln ala leu lys leu leu thr gln cys val
```

*FIG. 1B*

961
AAT ATG TCG CCA AAC AGC ATT GCG CCT TAC TGT GCG CTG GCA GAA TGC TAC CTC AGC ATG
asn met ser pro asn ser ile ala pro tyr cys ala leu ala glu cys tyr leu ser met
1021
GCG CAA ATG GGG ATT TTT GAT AAA CAA AAC GCA ATG ATC AAA GCT AAA GAA CAT GCG ATT
ala gln met gly ile phe asp lys gln asn ala met ile lys ala lys glu his ala ile
1081
AAG GCG ACA GAG CTG GAC CAC AAT AAT CCA CAA GCT TTA GGA TTA CTG GGG CTA ATT AAT
lys ala thr glu leu asp his asn asn pro gln ala leu gly leu leu gly leu ile asn
1141
ACG ATT CAC TCA GAA TAC ATC GTC GGG AGT TTG CTA TTC AAA CAA GCT AAC TTA CTT TCG
thr ile his ser glu tyr ile val gly ser leu leu phe lys gln ala asn leu leu ser
1201
CCC ATT TCT GCA GAT ATT AAA TAT TAT TAT GGC TGG AAT CTT TTC ATG GCT GGT CAG TTG
pro ile ser ala asp ile lys tyr tyr tyr gly trp asn leu phe met ala gly gln leu
1261/421
GAG GAG GCC TTA CAA ACG ATT AAC GAG TGT TTA AAA TTG GAC CCA ACG CGC GCA GCC GCA
glu glu ala leu gln thr ile asn glu cys leu lys leu asp pro thr arg ala ala ala
1321/441
GGG ATC ACT AAG CTG TGG ATT ACC TAT TAT CAT ACC GGT ATT GAT GAT GCT ATA CGT TTA
gly ile thr lys leu trp ile thr tyr tyr his thr gly ile asp asp ala ile arg leu
1381/461
GGC GAT GAA TTA CGC TCA CAA CAC CTG CAG GAT AAT CCA ATA TTA TTA AGT ATG CAG GTT
gly asp glu leu arg ser gln his leu gln asp asn pro ile leu leu ser met gln val

*FIG. 1C*

1441/481                                          1471
ATG TTT CTT TCG CTT AAA GGT AAA CAT GAA CTG GCA CGA AAA TTA ACT AAA GAA ATA TCC
met phe leu ser leu lys gly lys his glu leu ala arg lys leu thr lys glu ile ser
1501                                              1531
ACG CAG GAA ATA ACA GGA CTT ATT GCT GTT AAT CTT CTT TAC GCT GAA TAT TGT CAG AAT
thr gln glu ile thr gly leu ile ala val asn leu leu tyr ala glu tyr cys gln asn
1561                                              1591
AGT GAG CGT GCC TTA CCG ACG ATA AGA GAA TTT CTG GAA AGT GAA CAG CGT ATA GAT AAT
ser glu arg ala leu pro thr ile arg glu phe leu glu ser glu gln arg ile asp asn
1621                                              1651
AAT CCG GGA TTA TTA CCG TTA GTG CTG GTT GCC CAC GGC GAA GCT ATT GCC GAG AAA ATG
asn pro gly leu leu pro leu val leu val ala his gly glu ala ile ala glu lys met
1681                                              1711
TGG AAT AAA TTT AAA AAC GAA GAC AAT ATT TGG TTC AAA AGA TGG AAA CAG GAT CCC CGC
trp asn lys phe lys asn glu asp asn ile trp phe lys arg trp lys gln asp pro arg
1741                                    iagB
TTG ATT AAA TTA CGG TAA AAT CTG AGA GAG ATT ATG CAT TAT TTT TTT ATC ATC GTA
leu ile lys leu arg              met his tyr phe phe ile ile val
1800      553                         554
ATC TGG TTG CTT AGC ATA AAT AAT ACG GCA TGG GCT GAT TGC TGG CTT CAG GCT GAA AAA ATG
ile trp leu leu ser ile asn asn thr ala trp ala asp cys trp leu gln ala glu lys met
1860                                              1890
TTC AAT ATT GAA TCC GAA CTA CTT TAC GCT ATC GCC CAG CAG CAG GAA TCG GCG ATG AAA CCT
phe asn ile glu ser glu leu leu tyr ala ile ala gln gln gln glu ser ala met lys pro

*FIG. 1D*

1920
GGC GCC ATT GGT CAT AAC CGA GAT GGT TCA ACC GAT CTT GGC CTG ATG CAA ATT AAC AGC
gly ala ile gly his asn arg asp gly ser thr asp leu gly leu met gln ile asn ser
1980                                              1950
TTC CAT ATG AAA AGG CTG AAA AAA ATG GGG ATT AGT GAA AAA CAG TTG TTA CAG GAT CCC
phe his met lys arg leu lys lys met gly ile ser glu lys gln leu leu gln asp pro
2040                                              2010
TGC ATT TCT GTC ATT GTG GGC GCA TCC ATT TTA TCA GAT ATG ATG AAA ATC TAC GGT TTT
cys ile ser val ile val gly ala ser ile leu ser asp met met lys ile tyr gly phe
2100                                              2070
AGC TGG GAG GCC GTT GGC GCT TAT AAT GCC GGG ACG TCG CCG AAA CGA TCG GAT ATA AGG
ser trp glu ala val gly ala tyr asn ala gly thr ser pro lys arg ser asp ile arg
2160                                              2130
AAA CGT TAT GCT AAA AAA ATT TGG GAG AAT TAC AGA AAA TTA AAA GAG ATG TCA GCA GAA
lys arg tyr ala lys lys ile trp glu asn tyr arg lys leu lys glu met ser ala glu
2220                                              2190
GAG AAA AAC AAA AGA CTT TCT ATC GCG GTA AAC AAA TAA TTA TAC AGG AAT AGC TTA CTT
glu lys asn lys arg leu ser ile ala val asn lys
                                            713
2280                                              2250
TCA GAT AAT TCT AAA AGT AAG CTA TGT TTT TAT CAG CTT GCC GTC GTC ATA AGC AAC TGG
2340                                              2310
GCT TGC ATT GCT TTT AGT TGT ACA AAC TGT GAG GCG TCT TCC AGC ATT CTA TTG TTC CGT
2400                                              2370
GAA TTC

*FIG. 1E*

| | 1345 | | | | | | | | | | | | | | |
|---|---|---|---|---|---|---|---|---|---|---|---|---|---|---|---|
| SEQ | TAT | TAT | CAT | ACC | GGT | ATT | GAT | GAT | GCT | ATA | CGT | TTA | GGC | GAT | GAA | TTA | CGC | TCA | CAA | CAC |
| G1 | --- | --- | --- | --- | --- | --- | --- | --- | --- | --- | --- | --- | --- | --- | --- | --- | --- | --- | --- | --- |
| G2 | --- | --- | --- | --T | --- | --- | --- | --- | --C | --- | --- | --- | -A- | --- | --C | --- | --- | --T | --- | --- |
| G3a | --C | --- | --- | --- | G-- | --C | --- | --- | --- | --- | --- | --- | -A- | --- | --- | --- | --- | --T | --G | --- |
| G3b | --- | --- | --- | --- | --T | --C | C-- | --- | --- | --- | --- | --- | -A- | --- | --- | --- | --- | --- | --- | --T |
| G4 | --C | --- | --- | --- | G-T | --C | C-- | --- | --- | --- | --- | --- | -A- | --- | --- | --- | --- | --T | --- | T-T |
| G5 | --- | --- | --- | --- | --A | --C | C-- | --- | --- | --- | --- | --- | --- | --- | --- | --- | --- | -A- | --- | --T |
| G6 | --- | --- | --- | --- | --C | --- | --- | --- | --- | --- | --G | --- | -A- | --- | --- | --- | --- | --T | --- | --- |

| | | | | | | | | | | | | | | | |
|---|---|---|---|---|---|---|---|---|---|---|---|---|---|---|---|
| SEQ | CTG | CAG | GAT | AAT | CCA | ATA | TTA | TTA | AGT | ATG | CAG | GTT | ATG | TTT | CTT | TCG | CTT | AAA | GGT | AAA |
| G1 | --- | --- | --- | --- | --- | --- | --- | --- | --- | --- | --- | --- | --- | --- | --- | --- | --- | --- | --- | --- |
| G2 | --- | --- | --- | --- | --C | --- | --- | --- | --- | --- | --- | --- | --- | --- | --- | --T | --- | --- | --- | --- |
| G3a | --- | --- | --A | --- | --- | --T | C-- | --- | --- | --- | --- | --- | --- | --- | --- | --- | --- | --- | --- | --- |
| G3b | T-- | --- | --A | --- | --T | --- | --- | C-- | --- | --- | --- | --- | --- | --- | --- | --- | --- | --- | --- | --- |
| G4 | T-- | --- | --- | --- | --- | --- | --- | --- | --- | --- | --- | --- | --- | --- | --- | --- | --- | --- | --- | --- |
| G5 | T-- | --A | --- | --- | --- | --- | --- | --- | --- | --- | --- | --C | --- | --- | --- | --- | --- | --- | --- | --- |
| G6 | T-- | --A | --- | --- | --- | --- | --- | --- | --- | --- | --- | -A- | --- | --- | --- | --- | --- | --- | --- | --- |

| | |
|---|---|
| K.oxytoca | 2 Nyanza |
| K.pneumonia | 3 Poona |
| A.baumanii | 11 gpe II |
| P.mirabilis | 12 gpe II |
| S.marcescens | 18 gpe IIIa |
| E.agglomerans | 20 gpe IIIa |
| - | 21 gpe IIIb |
| Phi X174/Hae III | 30 gpe IIIb |
| M.avium | 31 gpe IV |
| M.tuberculosis | 35 gpe IV |
| L.monocytogenes | 36 gpe V |
| Témoin eau | 40 gpe V |
| Témoin eau | 45 gpe VI |
| Phi X174/Hae III | Phi X174/Hae III |

FIG. 5

SENSITIVITY

| number of copies | membrane hybridization | optical density microplate |
|---|---|---|
| 1 | | 0.020 |
| 5 | | 0.351 |
| 10 | | 1.912 |
| 50 | | 3.123 |
| 100 | | 3.200 |
| Control water | | 0.021 |

FIG. 6

OLIGONUCLEOTIDES FOR THE DETECTION OF SALMONELLA

BACKGROUND OF THE INVENTION

DESCRIPTION OF THE RELATED ART

The genus Salmonella contains two species, *Salmonella enterica*, a species divided into six sub-species on the basis of biochemical characteristics and those of homologies at the DNA level, and *Salmonella bongori*. The genus is subdivided into more than 2000 serovarieties defined with the aid of somatic and flagellar antigens. Bacteria of the genus Salmonella are generally pathogenic for animals and for man. It is thus known that Salmonella is among the agents responsible for the most common cases of food poisoning in developed countries; that is why rapid and reliable methods for the detection of subspecies of Salmonella are important.

The salmonellae responsible for food toxi-infections belong predominantly to the subspecies I (also called group I) of *S. enterica*.

Toxi-infections are however not the only pathologies caused by Salmonella infections.

For example, *Salmonella enterica* subspecies *enterica* serovariety *typhi* (called hereinafter *Typhi*) is the causative agent of human typhoid fever.

Given the nature of the infections caused by salmonellae and the need especially to search for their presence in biological samples taken from patients or from foods, it appears essential to have available rapid and sensitive means for detecting their presence therein.

The standard culture methods widely used up until now for the detection of salmonellae require a substantial amount of time and are not suitable for example for monitoring the contamination of food products. In order to overcome the disadvantages of these methods, several methods based on molecular biology techniques such as hybridization tests and tests based on the polymerase chain reaction have already been proposed. Various DNA probes have been used in several hybridization and PCR procedures to detect the Salmonella subspecies in the diet. However, none of these techniques is completely satisfactory since the sequences used are not completely known or are not exclusively present in the genus Salmonella and thus can lead to cross-reactions between the probe and DNA sequences from other enterobacteria or can lead to a large number of false negatives or false positives.

The inventors have sought means allowing the specific and sensitive detection of all the salmonellae of the species *S. enterica* and/or *S. bongori*. To this end, they focused their attention on the strain *Salmonella enterica* subspecies *enterica* serovariety *typhi* (*S. Typhi*) and on the gene involved in the invasion of cells by *S. Typhi*.

Furthermore, they defined certain conditions allowing the specific detection of defined groups of Salmonellae, for example Group I bacteria.

It has already been shown in the prior state of the art that the *Typhi* strain is capable of adhering to monolayers of HeLa cells and of entering into these cells (Yabuuchi et al, 1986). However, up until now, the genetic determinants involved in this process of adhering to and entering into the cells have not been clearly identified. Elsinghorst et al (1989) have cloned a *Typhi* chromosomal fragment which confers on *Escherichia coli* type bacteria the capacity to penetrate into Henle 407 cells. Recently, another chromosomal region involved in the invasion of HeLa cells by the *Typhi* Ty2 strain was identified and cloned (Popoff and Dion, 1990).

SUMMARY OF THE INVENTION

The inventors of the present application have identified on an *S. typhi* DNA fragment of 2.4 kb, contained in the HindIII sequence of 7.9 kb described by Popoff and Dion (1990), regions capable of taking part in the activity of invading *Salmonella enterica* subspecies enterica serovariety *Typhi* in cells, and in particular in HeLa type cell cultures, these regions being capable, in addition, of being used in reactions for carrying out a generalized diagnosis of all the representatives of the species *S. enterica* and/or *S. bongori* or optionally under special detection conditions, for the specific diagnosis of *S. enterica* group I.

A sequence called IagA and a sequence called IagB have been identified by the inventors and characterized as taking part in the cell invasion which manifests itself during an infection due to *Salmonella enterica* subspecies *enterica* serovariety *Typhi*.

The specificity of these sequences within *S. Typhi* has led the inventors to propose their use in order to define means for the diagnosis of an infection by *S. typhi* or even for the diagnosis of an infection by Salmonella of the species *S. enterica* and/or *S. bongori* or in certain cases for the detection of *S. enterica* of specific groups.

These means, which can be used for the diagnosis of an infection by *Salmonella enterica* and/or *Salmonella bongori* comprise oligonucleotides capable of being used in reactions for the amplification of nucleotide sequences, for example polymerase chain reactions. The invention also relates to probes for the detection of nucleic acids of *S. enterica* or of a specific subspecies of *S. enterica* and/or of *S. bongori*, these nucleic acids being, where appropriate, amplified fragments.

The subject of the invention is also a kit and a method for detecting the presence of *Salmonella enterica* and/or of *Salmonella bongori* in biological samples and for example in food products or in any sample which is the subject of a clinical diagnosis. These detection kits and methods are, according to a specific embodiment of the invention, specific for the group I strains of *S. enterica*.

According to another embodiment of the invention, these methods make it possible, on the contrary, to search for the presence of *S. enterica* or *S. bongori* bacteria of the genus Salmonella. The genus Salmonella thus comprises six subspecies or groups I, II, III, IV, V or VI. The subspecies I, II, III, IV and VI belong to the species *S. enterica* and the subspecies V belongs to the species *S. bongori*.

The invention also relates to the nucleotide sequences taking part in the invasion of cells by *Salmonella enterica* subspecies *enterica* serovariety *Typhi*, characterized in that they are one of the sequences iagA or iagB respectively between nucleotides 97 and 1755 of the sequence represented in FIG. 1 (IagA) and between nucleotides 1776 and 2255 of the sequence represented in FIG. 1 (IagB) (SEQ ID NO:1–3).

The invention also relates to nucleotide sequences which are modified in relation to iagA or iagB but exhibit nevertheless the same properties as regards the invasion of cells, or hybridize under stringent conditions with one of the abovementioned sequences.

The subject of the present application is also IagA and IagB proteins corresponding to the sequences presented in FIG. 1 or variants of these sequences which are obtained by mutation, deletion or addition of amino acids, as long as the sequence thus obtained is recognized by antibodies directed against one of the abovementioned IagA or IagB sequences (SEQ ID NO:2–3).

In general, the subject of the invention is any amino acid sequence encoded by the iagA and iagB genes represented in FIG. 1.

The invention relates, moreover, to any fragment especially any purified fragment of one of these sequences which is sufficient to allow *S. typhi* to preserve its properties of adhering and infecting cells, in particular HeLa cells in culture.

The process for infecting HeLa cells in culture is the standard process which has been especially described in the international patent application published under number WO 92/01056.

According to another aspect, the invention relates to means for detecting the presence of *S. enterica* and/or *S. bongori* and, where appropriate, for quantifying *S. enterica* and/or *S. bongori* in biological samples.

Biological sample is understood to mean any sample collected for carrying out in vitro analyses in animals or in man or collected from food products regardless of their nature or from any liquid, solid or gaseous medium likely to contain the desired pathogenic agents.

The subject of the invention in this context is a nucleotide sequence comprising at least 9 nucleotides, characterized in that it hybridizes with one of the IagA or IagB sequences presented above.

The hybridization conditions referred to above are defined according to the desired specificity of the hybridization and appropriate conditions are given as a guide in the examples of the present application.

Preferably, the invention relates to oligonucleotides derived from the C-terminal part of the iagA sequence represented in FIG. 1 (SEQ ID NO:1–2).

Oligonucleotide type sequences can be selected for use as primers either for the detection, after amplification, of the genomic DNA or the cDNA of Salmonella of the species *S. enterica* and/or of the species *S. bongori* belonging to the other groups I to VI or part of these groups, or under other conditions for the specific detection of *S. enterica* a group I. These may be especially nucleotide sequences obtained by chemical synthesis according to methods known to a person skilled in the art.

Preferred oligonucleotides which can be used for the amplification of nucleic acid characteristic of bacteria belonging to one of the groups I, II, IIIa, IIIb, IV, V or VI of the genus Salmonella and especially of the genomic DNA or the cDNA of *S. enterica* and/or of *S. bongori*, are for example the following (their position within the IagA sequence represented in FIG. 1 being indicated) (SEQ ID NO:4–14):

| | | position |
|---|---|---|
| Iag1: | 5'-TA TTA AGT ATG CAG GTT ATG-3' | 1424–1443 |
| Iag2: | 5'-AGA GAA TTT CTG CAA AGT GAA-3' | 1585–1605 |
| Iag3: | 5'-ATA TCC ACG CAG GAA ATA ACA GGA CTT-3' | 1495–1521 |
| Iag4: | 5'-GAG CGT GCC TTA CCG ACG ATA-3' | 1564–1584 |
| Iag5: | 5'-GCA GGG ATC ACT AAG CTG TG-3' | 1318–1337 |
| Iag6: | 5'-CGT GGG CAA CCA GCA CTA ACG-3' | 1637–1657 |
| S1m1: | 5'-CG GGT TAA AGG TTA TCA CCT-3' | 709–728 |
| S1m2: | 5'-AG CAT GGC GCA AAT GGG-3' | 1014–1031 |
| S1m3: | 5'-GCA CCA GGA AAG CAT TAA GTT GAT AGA ACA C-3' | 732–762 |
| S1m4: | 5'-CTT CGC TGG GAC ACA AAG CA-3' | 823–842 |
| SS28: | 5'-TAA TGC TTT CCT GGT GC-3'. | |

Other oligonucleotides capable of being used as primers for the amplification of DNA or of cDNA from the iagB gene of all Salmonella strains of the species *S. enterica* and/or of *S. bongori* have been defined from the iagB sequence represented in FIG. 1.

The subject of the invention is therefore the oligonucleotides corresponding to the following chains (SEQ ID NO:15–18):

Iag7: 5'-T ACG GCA TGG GCT GAT TGC T-3'
Iag8: 5'-T TAC GCT ATC GCC CAG CAG CAG GA-3'
Iag9: 5'-T GGT CAT AAC CGA GAT GGT TCA AAC GAT C-3'
Iag10: 5'-A CAG TTG TTA CAG GAT CCC T-3'

These oligonucleotides can also be used as probes, for example for the detection of the products of amplification of the DNA and/or of the cDNA of *S. enterica* and/or of *S. bongori.*

A pair of primers which is preferred for carrying out the amplification of the nucleic acid of *S. enterica* and/or of *S. bongori*, regardless of the group to which the bacterium belongs, is for example composed of the primers Iag5 (sense) and Iag6 (antisense).

This pair of primers direct the amplification of a 340 bp nucleic acid fragment.

Another preferred pair of primers is composed of the primers Slm1 (sense) and Slm2 (antisense). These primers are capable of hybridizing with the DNA or the cDNA of *S. enterica* and/or of *S. bongori* bacteria of one of the groups I, II, III, IV, V or VI.

According to another preferred embodiment, the invention relates to the oligonucleotides which can be used as primers for the specific detection of *Salmonella enterica* Group I when the detection conditions after the amplification of the DNA or of the cDNA are those which are described in example I.

Such primers are characterized by their capacity to amplify nucleic acid sequences from *S. enterica* or *S. bongori* strains representative of the groups I, II, III, IV, V and VI, but for which the detection conditions are those set out in example I allowing the detection of the group I bacteria alone.

A pair of oligonucleotides which can be used for these purposes, as primers specific for the detection of DNA or cDNA sequences from *S. enterica* group I for example consists of the following sequences (SEQ ID NO:19, 14):

SS2 5'-CCGGGCAGATGATACCC-3' and
SS28 '-TAATGCTTTCCTGGTGC-3'.

The oligonucleotides defined by the inventors make it possible to envisage the diagnosis of *S. enterica* and/or of *S. bongori* under satisfactory conditions in terms of sensitivity speed, ease and specificity.

The subject of the invention is also a kit for the detection of *S. enterica* and/or of *S. bongori* by amplification of the genomic or complementary DNA of *S. enterica* and/or of *S. bongori*, characterized in that it comprises:

- oligonucleotides as described above, which are capable of hybridizing under stringent conditions with the genomic DNA or the cDNA of *S. enterica* and/or of *S. bongori,* a probe for the detection of the amplified fragments corresponding to one of the definitions given in the preceding pages, the reagents necessary for carrying out the amplification reaction.

The subject of the invention is therefore in particular the use of the abovementioned oligonucleotides as primers for the amplification of a DNA or cDNA sequence from *Salmonella enterica* and/or from *Salmonella bongori*, which is contained in one of the iagA or iagB sequences as described in the preceding pages or which are complementary to such a sequence, or alternatively the use of these oligonucleotides as probe for the detection of an amplified nucleotide sequence.

For example, the oligonucleotides iag5 and iag6 can be used respectively as sense and antisense primers for the detection of *S. enterica* and/or of *S. bongori* of the group I, II, III, IV, V or VI.

Likewise, the pair of primers Slm1 and Slm2 can be used for the detection of bacteria of the species *S. enterica* and/or *S. bongori* from one of these groups in a biological sample.

The invention also relates to the use of the oligonucleotides SS2 and SS28 for the specific detection in vitro, in a biological sample, of *S. enterica* group I.

The detection is specific when the primers used for the amplification of the desired nucleotide sequences allow the amplification of *S. enterica* and/or *S. bongori* bacteria belonging to one of the other groups II, III, IV, V or VI, but that the conditions used do not allow the detection of bacteria of these same groups or of different organisms which are capable of being present in the biological sample tested.

The invention thus relates to a set of oligonucleotides which can be used for the detection of *S. enterica* and/or *S. bongori* bacteria after amplification of the genomic or complementary DNA of *S. enterica* and/or of *S. bongori*, characterized in that it comprises:

a pair of oligonucleotides corresponding to the definitions given above, which are capable of hybridizing under stringent conditions with the genomic DNA or the cDNA of *S. enterica* and/or of *S. bongori*, a probe corresponding to the characteristics given above.

A first set of oligonucleotides which can be used for the in vitro detection, in a biological sample, of *Salmonella enterica* and/or *S. bongori* strains belonging to one of the groups I, II, III, IV, V or VI, is characterized in that it contains the following oligonucleotides (SEQ ID NO:8–9):

the sequence Iag5 (5'-GCA GGG ATC ACT AAG CTG TG-3' and the sequence Iag6 (5'-CGT GGG CAA CCA GCA CTA ACG-3') which can be used as primers for the amplification and the sequence Iag3 (5'-ATA TCC ACG CAG GAA ATA ACA GGA CTT -3') which can be used as revealing probe and the sequence Iag4 (5'-GAG CGT GCC TTA CCG ACG ATA-3') which can be used as capture probe (SEQ ID NO:6–7).

Another set of oligonucleotides which can be used for the specific detection in vitro, in a biological sample, of *S. enterica* group I, is characterized in that it comprises the following oligonucleotides (SEQ ID NO:17–15):
SS2 (5'-CCGGGCAGATGATACCC-3' and
SS28 ('-TAATCGTTTCCTGGTGC-3').

The subject of the present application is moreover an iagA protein encoded by the nucleotide sequence iagA represented in FIG. 1, as well as a protein iagB encoded by the nucleotide sequence iagB represented in FIG. 1.

Preferably, the iagA and iagB proteins have respectively the amino acid sequences represented in FIG. 1.

Also entering within the framework of the invention is a process for the in vitro detection, in a biological sample, of *Salmonella enterica* and/or *S. bongori* nucleotide sequences previously amplified for example by PCR, characterized in that it comprises the steps of:

denaturing the amplified *S. enterica* and/or *S. bongori* sequence, bringing the denatured amplified nucleotide sequences from *S. enterica* and/or from *S. bongori* into contact with a capture probe and a revealing probe which are obtained from the oligonucleotides defined above under conditions allowing the hybridization of the said capture and revealing probes with the above-mentioned amplified nucleotide sequence from *S. enterica* and/or from *S. bongori*, the capture probe being attached to the surface of a well of a microtitre plate and the revealing probe being labelled and free in an appropriate hybridization buffer;

incubating the reaction mixture for a sufficient time to allow the hybridization reaction;

washing in order to remove the unreacted oligonucleotides;

revealing the revealing probes having hybridized to the amplified nucleotide sequences.

The detection process described above may be advantageously characterized in that the detection is carried out in accordance with the following steps:

denaturation of a 10 μl volume of the amplified sequence by addition, volume for volume, of a 200 mM NaOH, 40 mM EDTA solution, prehybridization of the microplates whose well surface is coated with the capture probe, in an appropriate hybridization buffer, release of the microplate and filling of each of the wells with 200 μl of hybridization buffer containing the denatured amplified fragment and the revealing probe labelled with peroxidase at the concentration of 10 ng/μl, incubation of the mixture for one hour at 37° C., with stirring, washing of the mixture which has reacted with a 10× washing solution (100 mM Tris, 3M NaCl, 1% Tween 20, pH 7.4), detection of the activity of the peroxidase linked to the probe by colorimetry in the presence of a colored substrate.

The revealing of the activity of the peroxidase present on the revealing probe can be obtained by carrying out the following steps:

deposition of 200 μl of a 40 mM trisodium citrate solution, 0.03% $H_2O$ 30%, 7.5 mg/ml of orthophenylenediamine (OPD) in each of the wells containing the reaction mixture, incubation of the microplate for 30 min in the dark and at 37° C., blocking of the reaction by addition of 50 μl/well of a 4N $H_2SO_4$ solution, determination of the optical density at a wavelength of 492 nm (reference at 620 nm).

Advantageously, the capture probe used is the oligonucleotide Iag4 and the revealing probe is the oligonucleotide Iag3.

Thus, the means defined within the framework of the invention allow the qualitative or quantitative detection of the presence of *S. enterica* and/or *S. bongori* type bacteria, whether this is a nonspecific detection within one of the groups I, II, III, IV, V or VI of *S. enterica* and/or of *S. bongori*.

Under specific conditions for carrying out the detection step, as set out in example I, the primers SS2, SS28 and the probe SS40 allow on the contrary the specific detection of *S. enterica* group I bacteria.

BRIEF DESCRIPTION OF THE DRAWINGS

Other characteristics and advantages of the invention appear in the following examples and in the figures:

FIG. 1: Nucleotide sequence of a 2.4 kb DNA fragment of the invasion region of *Salmonella ser. Typhi*.

The potential sites for binding to the ribosome are underlined (SEQ ID NO:1–3).

Figure 2:
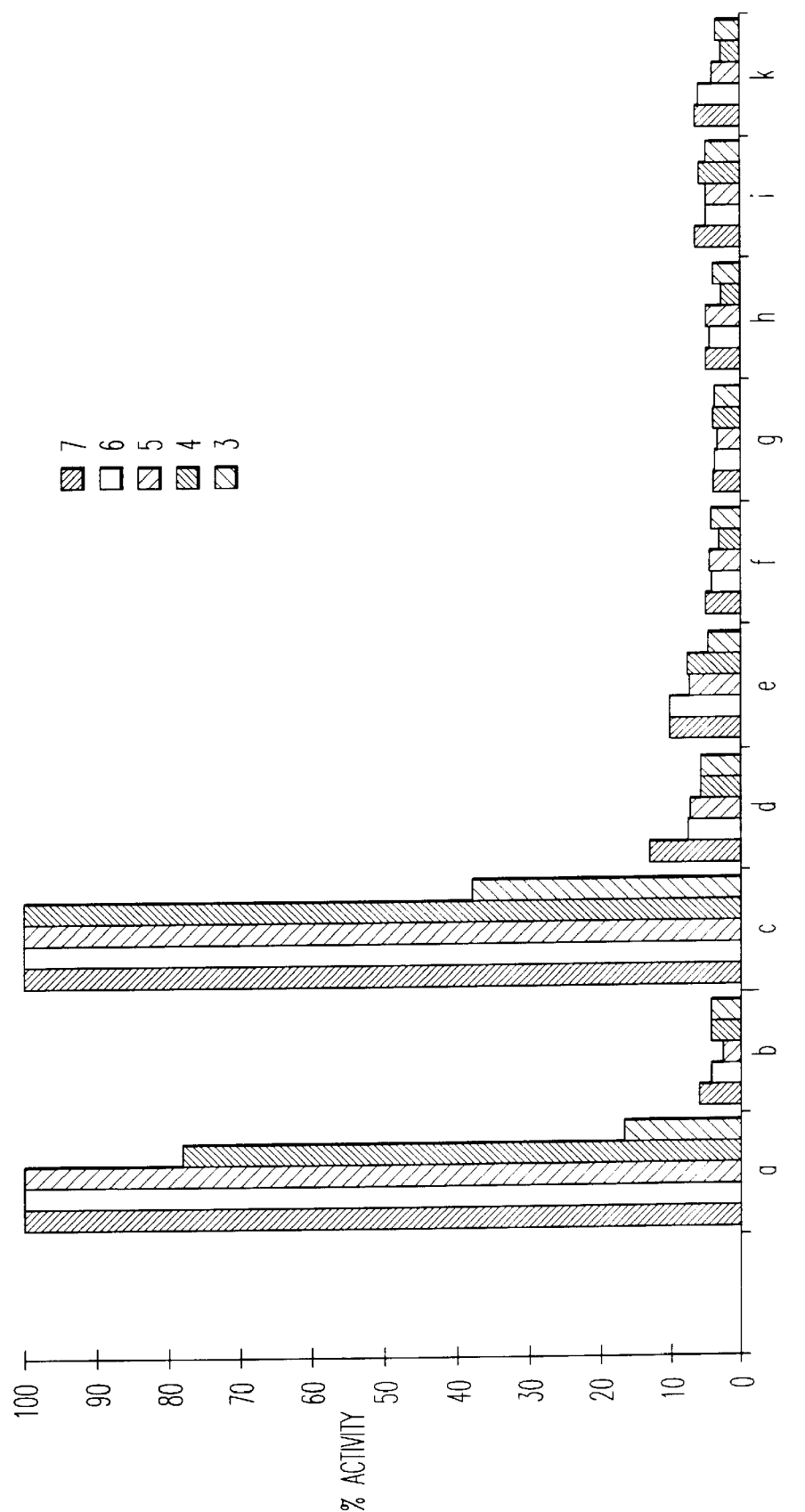

FIG. 2: Percentage of the activity obtained with various strains of Salmonella belonging to various serovarieties by sandwich hybridization. Serovarieties of various Salmonella isolates tested:

a: *S. enterica* subspecies *enterica* (1), ref.: C53
b: *S. enterica* subspecies *salamae* (II), ref.: 975–71
c: *S. enterica* subspecies *salamae* (II), ref.: 3975–83
d: *S. enterica* subspecies *arizonae* (IIIa), ref.: 1600K
e: *S. enterica* subspecies *arizonae* (IIIa), ref.: So 20—20
f: *S. enterica* subspecies *diarizonae* (II), (ref.: 5250–85
g: *S. enterica* subspecies *diarizonae* (IIIb), ref.: 8013–93
h: *S. enterica* subspecies *houtenae* (IV), ref.: 1357–73
i: *S. bongori*, ref.: 2790–79
k: *S. enterica* subspecies *indica* (VI), ref.: 4355–84—7, 6, 5, 4 and 3: log (amount of DNA molecules).

Figure 3B:
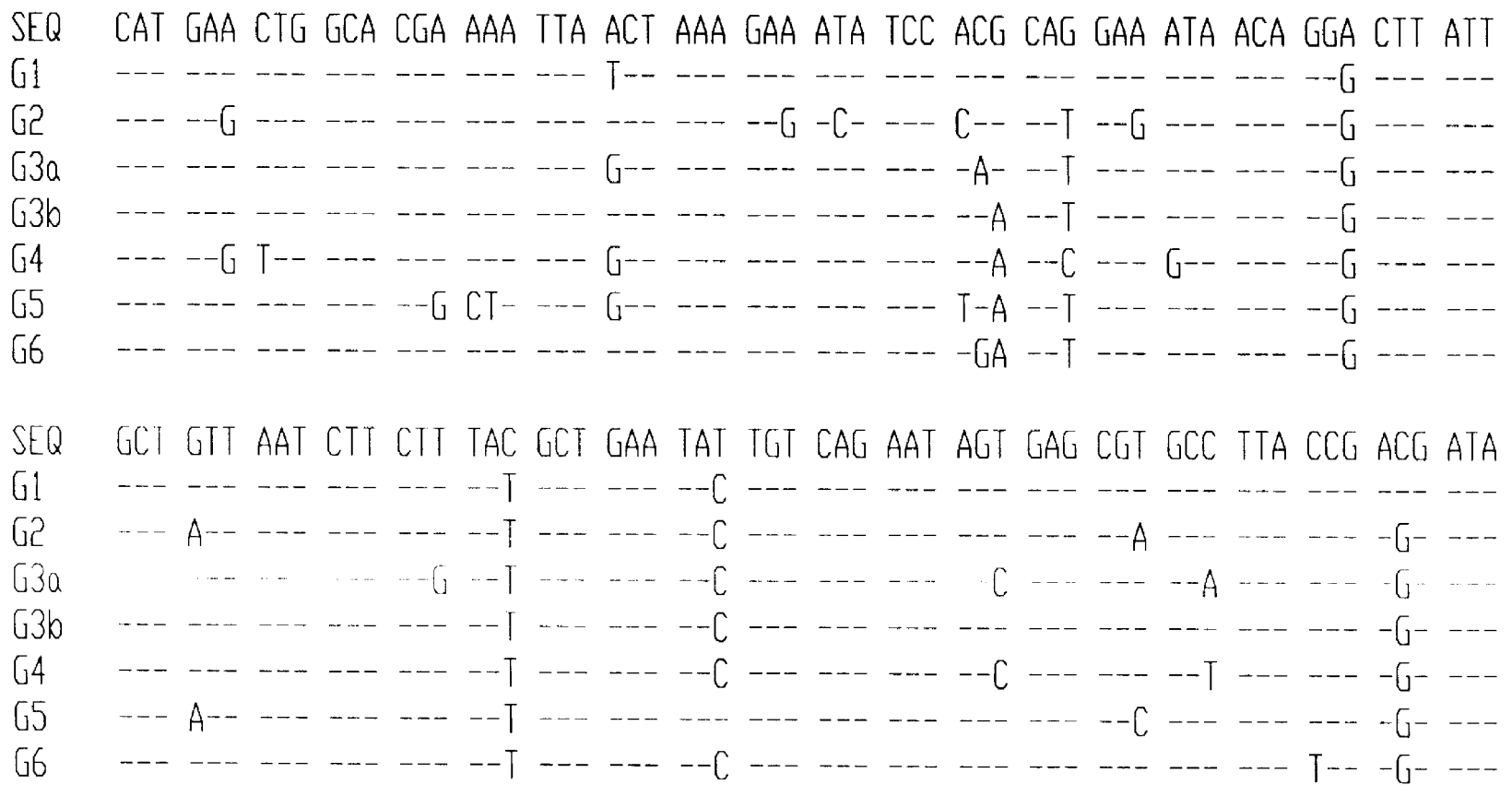

FIG. 3: Alignment of the sequences of the amplified fragments (nucleotides 1345 to 1644) of the 6 groups of Salmonellae (SEQ ID NO:20–27).

Figure 4:
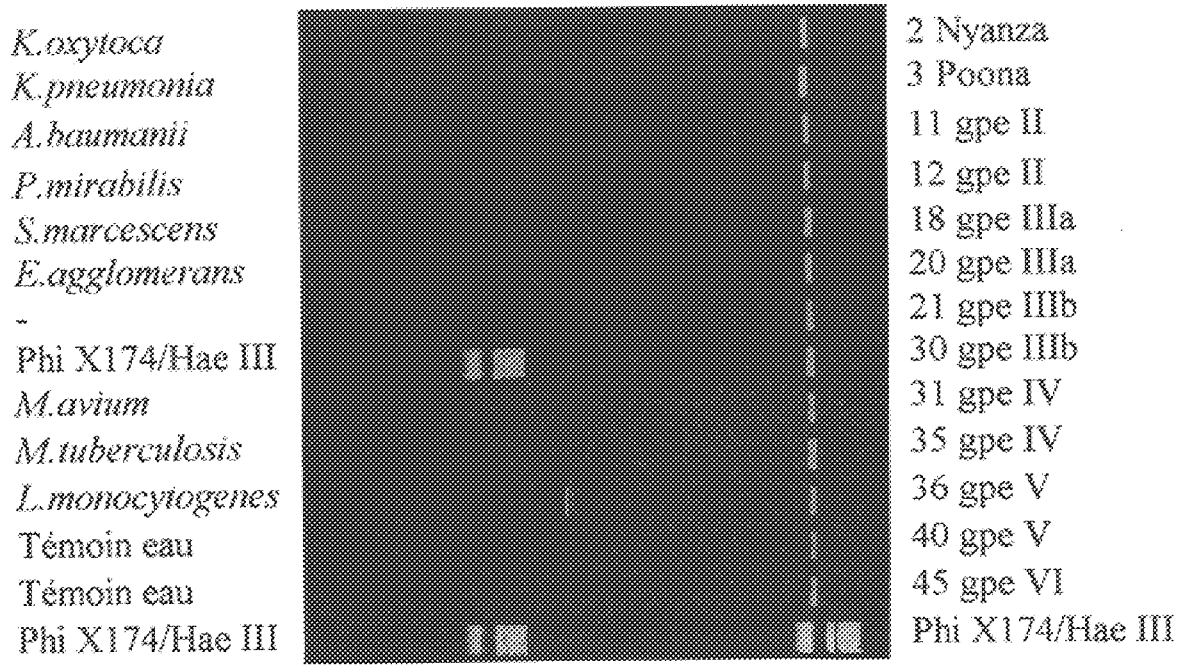

FIG. 4: Amplification by means of the primers Iag5 and Iag6 on two representatives of each of the groups of Salmonellae.

FIG. 5: Autoradiography of the Southern blot of the amplified products of Salmonellae.

FIG. 6: Determination of the minimum number of chromosomal DNA molecules which can be detected. Autoradiography of the Southern blot and microplate hybridization.

Figures 3C, 7:
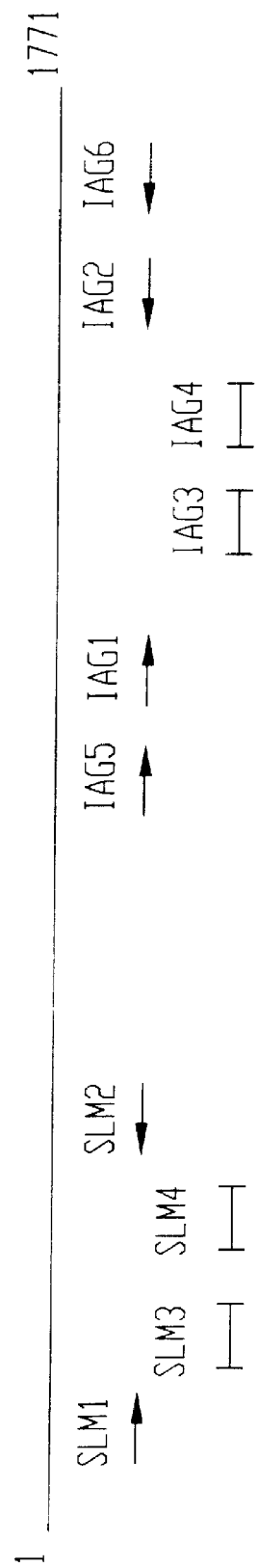

FIG. 7: Location of the oligonucleotides selected within the IagA gene.

EXAMPLE I

CLONING AND SEQUENCING OF THE 2.4 kb DNA FRAGMENT

DESCRIPTION OF THE PREFERRED EMBODIMENTS

This DNA fragment was subcloned using a restriction fragment obtained by cutting with the HindIII enzymes, from the 7.9 kb HindIII sequence described in the publication by Popoff and Dion, 1990, into derivatives of the vector m13 (Messing and Vieira, 1982).

After carrying out this cloning, the chain termination dideoxy method was carried out using the modified T7 DNA polymerase (Sequenase, USB Corp.) and universal synthetic oligonucleotides as primers. All the ends of the restriction fragments used overlap with each other. The sequencing of the DNA was carried out at least twice on each of the strands. The nucleotide sequence was analyzed using the Lipan and Pearson programme, 1985.

As shown by the sequence presented in FIG. 1, two open reading frames are contained in the fragment sequenced; they are designated by the terms iagA (abbreviation for invasion associate gene) and iagB. The two open reading frames are transcribed in the same orientation. The first ATG codon (bp 97) of the open reading frame of iagA which is preceded by the sequence 5'-AGAGA-3' is supposed to correspond to the site of initiation of translation of the iagA gene. The iagA gene encodes a polypeptide containing 553 amino acid residues with a calculated molecular weight of 63026 Da. A significant homology was detected between the N-terminal domain of the IagA protein and the domain corresponding to the protein for regulation of transcription PhoB (24% identity and 52% similarity for a superposition of 108 amino acids) and the protein PhoP (25% identity and 69% similarity for 100 aligned amino acids) of *E. coli*. The ATG codon for initiation of the iagB gene (bp 1776) is also preceded by a potential ribosome-binding site (5'-AGGAAG-3'). The iagB gene encodes a polypeptide containing 160 amino acids and having a calculated molecular weight of 18369 Da. Comparison of the sequence of the IagB protein with the translated sequences contained in the Genbank databank has shown a significant homology with the protein IpgF (43% identity and 66% similarity for 151 aligned amino acids).

The IpgF protein is encoded by the ipgF gene which is situated on the plasmid associated with the virulence of *Shigella flexneri*, at the 5' end of the mxi-spa locus (Allaoui et al, 1993).

The *Salmonella enterica* subspecies *enterica* serovariety Typhi proteins detected are therefore thought to have a role in the infection by these bacteria, and especially in the adhesion and the penetration into the cells.

EXAMPLE 2

SPECIFIC DETECTION OF *S. ENTERICA* GROUP I

A procedure for detecting the subspecies of Salmonella by the polymerase chain reaction (PCR) has been developed. A pair of oligonucleotides used as primer was defined in order to amplify a 93 bp fragment of a gene required for the invasion of HeLa cells by *S. typhi*, strain Ty2. The amplification product was analyzed by a nonradioactive sandwich hybridization on microtitre plates using two different oligonucleotides according to the procedure described by Chevrier et al, 1993, Mol. Cell. Probes 7, 187–197. The capture oligonucleotide was phosphorylated at its 5' end and covalently linked to wells carrying amine-containing groups of a microtitre plate. The detection oligonucleotide was aminated at its 5' end and then labelled with a biotinyl-N-hydroxy-succinimide ester. After hybridization, the hybrid molecules were detected by avidin conjugated to alkaline phosphatase and to a chromogenic substrate. This method requires the use of only a thermal cycler and a conventional microtitre reader, and can be carried out on a large scale.

MATERIALS AND METHODS

Bacterial strains

Two hundred and twenty-eight clinical isolates (Table 1) including *S. bongori* (Sambrook et al, 1989, Molecular cloning, a laboratory manual. Cold Spring Harbor Laboratory Press, Cold Spring Harbor, N.Y.), *S. enterica* subspecies I(116), II(56), IIIa(11), IIIb(30), IV(5) and VI(5) and 16 non-salmonella Enterobacteria strains (Table 2) representing 9 different genera were used in this study. The *S. ser. Typhimurium* C53 strain was used as positive control, and the *E. coli* HB101 strain was used as negative control in the PCR tests.

Extraction of DNA

The strains were cultured in an LB medium at 37° C. In order to carry out the rapid extraction of the DNA, 2 ml of the culture maintained overnight were centrifuged and resuspended in 1 ml of TE (10 mM Tris-HCl buffer at pH 8 containing 1 mM EDTA). The cells were centrifuged, the centrifugation pellet was resuspended in 500 µl of sterile distilled water and heated at 100° C. for 10 minutes. Finally, the solution was centrifuged and the supernatant was stored for the PCR experiments.

Oligonucleotide primers and probes

The oligonucleotides were synthesized in a cyclone DNA synthesizer (Millipore-Waters) using the phosphoramidite technology.

The sequences of the oligonucleotide primers were the following (SEQ ID NO:14, 19):
SS2: 5'-CCGGGCAGATGATACCC-3' and
SS28: 5'-TAATGCTTTCCTGGTGC-3'.

The capture oligonucleotide probe,
SS40: 5'-CCCGAACTATCTCGATCTGTACAATATTAT-CATT-3' was phosphorylated at its 5' end with T4 polynucleotide kinase (Boehringer) according to the description made by Sambrook et al, 1989, (Molecular cloning, a laboratory manual. Cold Spring Harbor Laboratory Press, Cold Spring Harbor, N.Y.) (SEQ ID NO:28). The octadecanucleotide detection probe SS41 (5'-GCAGGTGATAACCTTTAA-3') was synthesized with an amino functional group at its 5' end using the solid phase phosphoramidite method in an Applied Biosystem 380B DNA synthesizer and then labelled with D-biotinyl-Σ-aminocaproic acid-N-hydroxysuccinimide ester (Boehringer) according to the description made by Tham et al, 1990, (FEMS Microbiol. Lett. 69, 109–116) (SEQ ID NO:29). The capture and detection oligonucleotides were both purified on a rapid HR 10/10 desalting column with the FPLC system (Pharmacia).

PCR experiments

The DNA fragment subjected to the PCR reaction was denatured directly in the wells by adding sequentially 95 µl of distilled water, 5 µl of PCR sample, 40 µl of detection probe and 14 µl of 1N NaOH per well. After 10 minutes, neutralization was carried out by adding 21 µl of 1M NaH$_2$PO$_4$ containing 1% sarkosyl. All the samples were prepared in duplicate. After the neutralization, the band was deposited on a metallic surface and maintained in an oven overnight at 40° C. The final concentration of the biotinylated detection probe SS41 was 0.5 nM. During the incubation in the oven, it is preferable not to leave the unused wells empty but to fill them with water so as to obtain homogeneous thermal exchanges. The microwells were washed 5 times at room temperature with TBS-Tw (0.15M NaCl, 10 mM Tris-HCl buffer at pH 8, 1% Tween 20). 100 µl of alkaline phosphatase-extravidine conjugate (Sigma), diluted at 1 µg/ml in TBS-Tw containing 1% bovine serum albumin, were added per well. Next, the band was incubated at room temperature for 1 h, washed 5 times with TBS-Tw and finally 200 µl of 1M diethanolamine at pH 9.8 containing 1 mM MgCl$_2$ and 1 mM para-nitrophenyl phosphate were added. The enzyme reaction was carried out for 30 minutes to 2 hours. The absorbance was measured at 405 nm using a microplate reader (Dynatech). The signal obtained with the standard solution of the amplified DNA fragment (800 fm/well) of *S. ser. Typhimurium* strain C53 was considered to represent 100% and used as reference for each hybridization test. The blank values correspond to the mean absorbance measured in the wells coated with the oligonucleotide SS40 incubated with only 0.5 nM of biotinylated oligonucleotide probe SS41.

RESULTS

Optimization of the method

The primers and the probes were chosen in the iagA sequence. Various pairs of primers were tested in order to optimize the sandwich hybridization technique on CovaLink microplates. The pair of primers chosen (SS2 and SS28) allowed the specific amplification of the 93 bp region of the Salmonella genomic DNA. By using this pair of primers, it was shown that a standard MgCl$_2$ concentration (1.5–2 mM) led to a relatively unadvantageous amplification result and that an MgCl$_2$ concentration of 4 mM was necessary in order to obtain an efficient amplification. Internal oligonucleotides, SS40 and SS41, were used in a nonradioactive hybridization test as capture probe and detection probe respectively.

Specificity of the technique

The specificity of the method for the detection of salmonellae was evaluated with 228 strains of Salmonella (Table 1) and 16 heterologous bacteria strains (Table 2). The results are summarized in Table 3. *Edwardsiella tarda, Klebsiella pneumoniae*, species of *Enterobacter* and *Acinetobacter, Pasteurella, Vibrio harveyi, Serratia marcescens* and more substantially species of *Citrobacter* and all *E. coli* gave a hybridization signal of less than 20%. On the basis of this value, it was concluded that all the Salmonella strains belonging to the subspecies I could be detected by the present method. Furthermore, only one strain (strain 3975–83) of the 56 strains of the subspecies II and 3 strains of the 11 strains of the subspecies IIIa gave a positive signal. *Salmonella bongori* and the strains belonging to the subspecies IIIb, IV and VI were not detectable.

Detection level of the technique with whole bacteria $^1\!/_{10}$th dilutions of a suspension of the *S. ser. Typhimurium* C53 strain (from $10^9$ to $10^{-2}$ cells/ml) were made in order to estimate the minimum number of bacteria which could be detected by PCR followed by the nonradioactive hybridization technique. DNA was extracted from each calibrated suspension using the technique of rapid extraction by boiling. The results obtained show clearly that the technique of rapid extraction of DNA by simply boiling the suspension before the PCR reaction is an efficient technique. Indeed, it allows the detection of only one cfu unit.

TABLE 1

Salmonella subspecies used to evaluate the specificity of the DNA hybridization tests.

| Microorganism tested | No. of isolates | No. of serovars |
|---|---|---|
| *Salmonella enterica* subsp *enterica* I | 116 | 43 |
| serovar  Adelaide | | 1 |
| Agona | | 2 |
| Altona | | 1 |
| Angoda | | 1 |
| Bardo | | 2 |
| Blockley | | 1 |
| Bovismorbificans | | 3 |
| Braenderup | | 4 |
| Brandenburg | | 1 |
| Bredeney | | 1 |
| Broughton | | 2 |
| Cerro | | 1 |
| Chester | | 1 |
| Coeln | | 1 |
| Concord | | 1 |
| Dakar | | 1 |
| Derby | | 2 |
| Enteridis | | 28 |

TABLE 1-continued

Salmonella subspecies used to evaluate the specificity of the DNA hybridization tests.

| Microorganism tested | No. of isolates | No. of serovars |
|---|---|---|
| Georgia | | 1 |
| Hadar | | 1 |
| Heidelberg | | 4 |
| Ibadan | | 2 |
| Indiana | | 1 |
| Infantis | | 5 |

TABLE 2

Heterologous bacteria used in the DNA hybridization test

| Genus | Species | Number of isolates |
|---|---|---|
| Escherichia | coli | 4 |
| Edwarsiella | tarda | 1 |
| Citrobacter | amalonaticus | 1 |
| | freundii | 1 |
| Klebsiella | pneumoniae | 1 |
| Enterobacter | agglomerans | 1 |
| | asburiae | 1 |
| | hormoechei | 1 |
| Pasteurella | multocida | 1 |
| Acinetobacter | lwoffii | 1 |
| | haemolyticus | 1 |
| Vibrio | harveyi | 1 |
| Serratia | marcescens | 1 |

TABLE 3

Clinical strains of bacteria and controls tested in a Sandwich hybridization test

| activity (%) | S. enterica subsp. enterica | S. enterica subsp. salamae | S. enterica subsp. arizonae | S. enterica subsp. diarizonae | S. enterica subsp. houtenae | S. enterica subsp. indica | S. bongori | Non-Salmonella | Control without DNA |
|---|---|---|---|---|---|---|---|---|---|
| 100%–20% | 116 | 1 | 3 | 0 | 0 | 0 | 0 | 0 | 0 |
| 19% > blank | 0 | 51 | 8 | 12 | 4 | 4 | 5 | 9 | 0 |
| < blank | 0 | 4 | 0 | 18 | 1 | 1 | 0 | 7 | 23 |
| Total | 116 | 56 | 11 | 30 | 5 | 5 | 5 | 16 | 23 |

TABLE 1-continued

Salmonella subspecies used to evaluate the specificity of the DNA hybridization tests.

| Microorganism tested | No. of isolates | No. of serovars |
|---|---|---|
| Lexington | | 1 |
| London | | 1 |
| Mbandaka | | 1 |
| Montevideo | | 6 |
| Moscow | | 1 |
| Ohio | | 1 |
| Orion | | 1 |
| Panama | | 3 |
| Paratyphi B | | 2 |
| Saintpaul | | 1 |
| Typhimurium | | 13 |
| Typhisuis | | 1 |
| Vaertan | | 1 |
| Veneziana | | 1 |
| Vinohrady | | 1 |
| Virchow | | 10 |
| Wien | | 1 |
| Woodinville | | 1 |
| Yolo | | 1 |
| *Salmonella enterica* subsp *salamae* II | 56 | 56 |
| *Salmonella enterica* subsp *arizonae* IIIa | 11 | 29 |
| *Salmonella enterica* subsp *diarizonae* IIIb | 30 | 5 |
| *Salmonella enterica* subsp *houtenae* IV | 5 | 5 |
| *Salmonella enterica* subsp *indica* VI | 5 | 5 |
| *Salmonella bongori* (initially *S. enterica* subsp *bongori* V) | 5 | 5 |

Quantitative hybridization with purified genomic DNA

The nonradioactive hybridization procedure used in the tests reported here can be easily carried out in quantitative studies. To compare the hybridization signals obtained with various Salmonella strains, DNA was extracted from 10 strains representing the 6 subspecies of *Salmonella enterica* and the species *Salmonella bongori*, then calibrated quantities of DNA were subjected to PCR reactions followed by a sandwich hybridization. The results are reported in FIG. 2. It was demonstrated that the hybridization signal obtained with $10^7$ molecules of DNA of *Salmonella bongori* or of the subspecies II, IIIa, IIIb, IV and VI of *Salmonella enterica* is lower than the hybridization signal observed with $10^3$ molecules of DNA of the strains of the subspecies I. However, it is important to note that the isolate 3975–83 (subspecies II) gave the same hybridization signal as the strains belonging to the subspecies I.

DISCUSSION

PCR amplification allows a very sensitive detection of specific DNA sequences. The sensitivity of the amplification depends essentially on the number of copies of target DNA, the purity of the sample to be analyzed, the DNA extraction method, and the sensitivity of the method used to detect the PCR products. Visualization of the PCR products by ethidium bromide staining in an electrophoresis gel is not compatible with the routine use of the technique and is not sufficiently sensitive. The sensitivity can be enhanced by the use of double PCR or of DNA probes with a Dot-blot or a Southern-blot hybridization. However, double PCR is very sensitive to contamination by DNA and the Dot-blot or Southern-blot hybridization techniques are not appropriate for automation. Microplate hybridization therefore offers an appropraite technique for the detection and quantification of fragments amplified by PCR. The simple covalent attachment of the nucleic acids to microwells represents an advantageous variant of passive adsorption and a substantial improvement for the detection of fragments amplified by PCR on micro-wells.

It is known that the strains of Salmonella which cause infections in man belong essentially to the subspecies I. Indeed, more than 95% of the clinical isolates in humans belong to this subspecies (Rowe, B., 1987, Salmonella surveillance. Reports received from centers participating in the WHO programme. World Health Organization London). Furthermore, in 1991, the "Centre National d'Etudes Vétérinaires et Alimentaires" of Paris (France) reported [Corbion, B. et al, 1991, Inventory of Salmonella] that in the previous years, most of the strains isolated in animals in the diet or in the environment in 1988 and 1989 (that is to say, 18832 strains) belong to the subspecies I (99.2%).

The results reported here have made it possible to define a method based on PCR amplification for the detection of pathogenic strains of Salmonella. A pair of primers, SS2 and SS28, and a pair of probes, SS40 and SS41 were selected from a gene necessary for the invasion of HeLa cells by Salmonella ser. *Typhi* strain Ty2. By using the combination of the PCR technique and microplate nonradioactive sandwich hybridization, all the Salmonella bacteria of the subspecies I were detected.

The detection limit was lower than a threshold represented by 10 cells per PCR tube, which is in accordance with the results obtained by other similar PCR techniques. Given the nucleic acid similarity between members of the enterobacteria, it was important to check the specificity of these new primers and probes with the enterobacteria genera which are most likely to lead to "false-positive" type reactions. From the results obtained, it can be concluded that no false-positive reaction can take place when the PCR and hybridization conditions described above are followed.

It is advantageous to note that the Salmonella strain 3975–83 (subspecies II) had a hybridization signal identical to that obtained with the isolates belonging to the subspecies I. This strain was isolated in 1983 from stools from a human patient in Great Britain. On the basis of the biochemical characteristics, this new serovariety was classified in the subspecies II but was considered as an atypical strain since its presence was not detected in gelatinase (Le Minor, L. et al, 1984, Supplement No. XXVII, 1983, to Kauffmann-White Scheme, Ann. Microbiol. (Institut Pasteur) 135 B, 45–51). In the light of the results reported here, the taxonomic position of the strain 3975–83 ought to be reexamined using the DNA—DNA hybridization technique.

The data presented here indicate that the hybridization method based on the use of a gene necessary for the invasion of HeLa cells by Salmonella ser. *Typhi* strain Ty2 can distinguish the Salmonella strains of the subspecies I from the other enteric bacteria, including *E. coli*. The nonradioactive hybridization on a Covalink NH microplate is sensitive and appropriate for the analysis of a large number of samples.

EXAMPLE 3

DETECTION OF SALMONELLA DNA AMPLIFIED BY SANDWICH HYBRIDIZATION

Sequence of the oligonucleotides

The DNA fragments chosen are the following (SEQ ID NO:4–13) (see position on the sequence of FIG. 1):
C-terminal part

|  |  | position |
|---|---|---|
| Iag1: | 5'-TA TTA AGT ATG CAG GTT ATG-3' | 1424–1443 |
| Iag2: | 5'-AGA GAA TTT CTG CAA AGT GAA-3' | 1585–1605 |
| Iag3: | 5'-ATA TCC ACG CAG GAA ATA ACA GGA CTT-3' | 1495–1521 |
| Iag4: | 5'-GAG CGT GCC TTA CCG ACG ATA-3' | 1564–1584 |
| Iag5: | 5'-GCA GGG ATC ACT AAG CTG TG-3' | 1318–1337 |
| Iag6: | 5'-CGT GGG CAA CCA GCA CTA ACG-3' | 1637–1657 |
| Slm1: | 5'-CG GGT TAA AGG TTA TCA CCT-3' | 709–728 |
| Slm2: | 5'-AG CAT GGC GCA AAT GGG-3' | 1014–1031 |
| Slm3: | 5'-GCA CCA GGA AAG CAT TAA GTT GAT AGA ACA C-3' | 732–762 |
| Slm4: | 5'-CTT CGC TGG GAC ACA AAG CA-3' | 823–842 |

Preferably, the pair of primers Iag5 (sense) and Iag6 (antisense) directs the amplification of a 340 bp fragment, the pair Slm1 (sense) and Slm2 (antisense) directs the amplification of a 323 bp fragment (FIG. 3) (SEQ ID NO:8–11).

FIG. 4 shows the efficiency of the amplification of a pair of primers Iag5 and Iag6 on 2 representatives of each of the groups of Salmonellae (SEQ ID NO:8–9).

Process of detection

A format for detection by sandwich hybridization was used.

Two oligonucleotides hybridize simultaneously to the denatured amplified fragment. One of them, called capture probe, is attached passively (but can also be attached covalently) to the surface of a 96-well microtitre plate well. The other, called revealing probe, is labelled with an element which is easy to detect. The revealing probe is free in the hybridization buffer.

The capture and revealing probes are complementary to 2 different regions situated inside the amplified fragment.

The detection probe in the case described here is linked to an enzymatic marker, especially a peroxidase, and will serve as revealing probe. This is the case preferably for the oligonucleotides Iag3 and Slm3 (SEQ ID NO:6, 12). Other oligonucleotides can be attached to a microplate-type solid support, a particulate or membrane support and serve as capture probe, this particularly for the oligonucleotides Iag4 and Slm4 (SEQ ID NO:7, 13).

Experimental conditions

1) Preparation of the Salmonella DNA

Using the boiling method in the presence of Chelex (6% Chelex, 0.1% SDS, 1% NP40, 1% Tween 20), the DNA sequences are obtained. This reagent is marketed by Biorad and is used according to the manufacturer's procedure (ref. Walsh et al. 1991. BioTechniques 10: 506–513).

2) Amplification

According to the method initially described by Saiki and as set out, for example, in European Patent EP 0,201,184.

The PCR is carried out using the following reaction mixture:

50 mM KCl 10 mM Tris-HCl pH 8.3

1.5 mM $MgCl_2$

125 μM deoxyribonucleotides (dCTP, dATP, dGTP)

250 μM UTP 25 pmol of each of the primers 10 ng DNA 1 unit of Uracyl N Glycosylase 1 unit of Taq polymerase.

The reaction mixture was prepared using 10 μl of the solution containing the DNA to be amplified in a volume of 100 μl. The dUTP and UNG are used in a decontamination system (Brevet Life Technologies European Patent Application 0 401 037). The thermocycler used is Perkin Elmer 9600.

After incubation at 50° C. for 2 min in order to allow the action of the UNG and denaturation at 95° C. for 5 min, the temperature cycles used are the following:

5 cycles (95° C. 15 sec, 50° C. 15 sec, 72° C. 15 sec)
35 cycles (95° C. 15 sec, 57° C. 15 sec, 72° C. 15 sec)

3) Visualization of the amplification reaction 3-1) Labelling of the revealing probe The probes are labelled with horseradish peroxidase (ref. PCR protocols : a guide to methodes and application; Academic press (1990), 15, p4513–4534) and the activity of the enzyme is revealed by colorimetry.

3-2) Agarose gel stained with BET and membrane hybridization

After amplification, 10 μl of the amplification product are deposited on an agarose gel and the DNA is transferred onto a membrane according to conventional techniques (Maniatis). The membrane is prehybridized, 30 min at 68° C. in hybridization buffer (10×Denhart, 6×SSC, 0.1% SDS) and then hybridized at 42° C. for 3 h with 60 ng of probe per ml of hybridization buffer.

Washing is then carried out according to the following steps:

twice 10 min in 2×SSC–0.1% SDS at room temperature,
once 30 min in 0.1×SSC–0.1% SDS at 42° C.,
twice 10 min in 2×SSC at room temperature.

Revealing: The membrane is blotted between two sheets of absorbent paper (Whatman 3MM paper) and placed in a clean and dry tank.

The Amersham detection reagent (ECL RPN 2105 detection reagent) is prepared immediately before use volume for volume; 30 ml of total volume for a 5×8 cm membrane. A cassette for autoradiography is obtained by fixing a sheet of absorbent paper (Whatman 3MM paper) at the bottom. All these steps can be carried out under light, and then in a dark chamber.

The membrane is immersed in the detection reagent for 1 min, the DNA side on top, the membrane is drained rapidly, it is placed in the cassette, the DNA side on top, a sheet of transparent plastic is placed on top (otherwise the membrane sticks to the film) and an X-ray film is placed on top (X-OMAT KODAK film).

The exposure is carried out for 30 min at room temperature and then the film is developed by conventional developing techniques (developer, water, fixing agent).

3-3) Microplate 3-3-1) Coating of the capture oligonucleotide

It can be carried out by adsorption (Cook et al, NAR, 16: 4077–4095 (1988) or by covalent coupling (Rasmussen, S.R. et al, 1991. Analytical Biochemistry 198, 138–142).

3-3-2) Microplate hybridization and reading

10 μl of the amplification product were denatured by adding volume for volume a 200 mM NaOH, 40 mM EDTA solution.

The microplates in which the surface of the wells is coated with the capture probe were prehybridized in a hybridization buffer containing 10×Denhart, 6×SSC, 0.1% SDS.

Next, the microplate was emptied and each of the wells received 200 μl of hybridization buffer containing the denatured amplified fragment and the revealing probe at the concentration of 10 ng/μl. The incubation took place for one hour at 37° C. and with stirring.

After washing (10× washing solution: 100 mM Tris, 3M NaCl, 1% Tween 20, pH 7.4), the activity of the peroxidase linked to the probe was detected by colorimetry in the presence of a colored substrate.

To do this, 200 μl of a 40 mM trisodium citrate solution, 0.03% $H_2O$ 30%, 7.5 mg/ml of orthophenylenediamine (OPD) were distributed in each of the wells. The microplate was incubated for 30 min in the dark and at 37° C. 50 μl/well of a 4N $H_2SO_4$ solution were added in order to block the reaction.

The optical density was determined at a wave-length of 492 nm (reference at 620 nm).

4) Sequencing of the PCR products and manual alignment of the sequences.

According to conventional techniques, by using for example an Applied Biosystem "373 DNA sequencer" automatic machine and the Applied "dye terminator" kit.

Results

The exemplified model is preferably the following oligonucleotide system:

Iag5 sense primer-Iag6 antisense primer

Iag3 revealing probe and Iag4 capture probe (SEQ ID NO:8, 9, 6, 7).

(it should be noted that Iag4 can equally well be labelled and used as revealing probe).

Specificity study

It was performed on all of the bacterial strains listed in Tables 4 and 5.

The amplification of the DNA extracted from the 45 Salmonella strains tested generated a fragment of the expected size (cf. FIG. 5). The Southern blots of all the amplified products were hybridized with the internal oligonucleotide probe Iag3 labelled with peroxidase (SEQ ID NO:6). None of the non-salmonella strains gave rise to hybridization with a peroxidase probe obtained on a membrane according to the procedure described above.

The same amplification products were tested in a mircoplate format.

The cut-off was arbitrarily set at 0.050. All the representatives of each of the Salmonella groups give an optical density value greater than 0.050 (Table 6).

Sensitivity

In order to determine the minimum number of molecules of salmonella chromosomal DNA which can be detected, a range of dilution of purified chromosomal DNA was amplified. 5 molecules are visible on the southern blot autoradiograph and detected by microplate hybridization: the value obtained by colorimetry is greater than the Cut-Off (FIG. 6).

The oligonucleotides selected for carrying out this example are located on the sequence of the IagA gene (FIG. 7).

TABLE 4

SALMONELLA STRAINS STUDIED

| No. | Strains | Serotype | Group |
|---|---|---|---|
| 1 | Salmonella Marseille | | I |
| 2 | Salmonella Nyanze | | I |
| 3 | Salmonella Poona | | I |
| 4 | Salmonella Kampala | | I |
| 5 | Salmonella Taksony | | I |
| 6 | Salmonella Teshie | | I |
| 7 | Salmonella Indiana | | I |
| 8 | *Salmonella enteritidis* | | I |
| 9 | Salmonella Kentucky | | I |
| 10 | Salmonella Napoli | | I |
| 11 | | 841 11: a: d: en 215 | II |

TABLE 4-continued

SALMONELLA STRAINS STUDIED

| No. | Strains | Serotype | Group |
|---|---|---|---|
| 12 | | 1703K 41: 2: 15 | II |
| 13 | | 950-71 43: d: z 39 | II |
| 14 | | 10–65 44: 24, 223: - | II |
| 15 | | 3209-81 45: z 23 | II |
| 16 | | 5331/86 62: z 29: - | IIIa |
| 17 | | 3064-4/252 41: k: - | IIIa |
| 18 | | 594-54 38: z 54: - | IIIa |
| 19 | | 1694 cdai 426 63: z 4, z32: - | IIIa |
| 20 | | So 50/16 62: f, z 51: - | IIIa |
| 21 | | 5251-85 58: r: z 53 | IIIb |
| 22 | | 1758-76 6, 14: z 10: enx 215 | IIIb |
| 23 | | 453-68 16: liv: z 53 | IIIb |
| 24 | | 4305-57 16: li(v): z 35 | IIIb |
| 25 | | 1698-75 11: liv: z | IIIb |
| 26 | | 8275-94 47: r: enx 215 | IIIb |
| 27 | | 8283-94 53: z 10: z | IIIb |
| 28 | | cdc 456-5/93 40: i: 1, 5, 7 | IIIb |
| 29 | | 8284-94 60: i: z | IIIb |
| 30 | | 1693K 38: k: z 55 | IIIb |
| 31 | | 1707 48: f: z 51: - | IV |
| 32 | | 7231/89 45: z 36, z 38 | IV |
| 33 | | 6887/60 48: f, z 51: - | IV |
| 34 | | 1357/73 43: z 4, z 24: - | IV |
| 35 | | 1550K 16: z 4, z 23: - | IV |
| 36 | Salmonella Bongor | 261-66 48: z 35: - | V |
| 37 | Salmonella Camdeni | 2022-77 44: r: - | V |
| 38 | | 4985-85 48: z 39: - | V |
| 39 | | 7688-9166: z 39: - | V |
| 40 | | 1387–7340: a: - | V |
| 41 | | 1941-77 6, 7: z 41: 1, 7 | VI |
| 42 | | 1449K 45: a enx | VI |
| 43 | | 4355-84 1, 6, 14, 25: a: e, n, x | VI |
| 44 | | 1711K 11: b: enx | VI |
| 45 | | 1688K 1, 6, 14, 25: Z 10: 1, 12, 7 | VI |

TABLE 5

NON-SALMONELLA STRAINS

| No. | Name | Identification |
|---|---|---|
| 1 | Klebsiella oxytoca | 0059 SDP |
| 2 | Klebsiella pneumoniae | 0054 SDP |
| 3 | Acinetobacter baumanii | 0033 SDP |
| 4 | Proteus mirabilis | RP402 |
| 5 | Serratia marcescens | 0042 SDP |
| 6 | Enterobacter agglomerans | 0067 SDP |
| 7 | Citrobacter diversus | 0068 SDP |
| 8 | Pseudomonas aeruginosa | 0011 SDP |
| 9 | Enterobacter aerogenes | 0066 SDP |
| 10 | Escherichia coli | 0131 SDP |
| 11 | Enterocoque faecalis | 76117 |
| 12 | Proteus mirabilis | AP03 |
| 13 | Enterocoque faecalis | 76117 |
| 14 | Enterobacter cloacae | 0060 SDP |
| 15 | Mycobacterium avium | 6 |
| 16 | Mycobacterium tuberculosis | H 37 RV |
| 17 | Listeria monocytogenes | 1/2 LG3 |

TABLE 6

MICROPLATE DETECTION

| SAMPLES | OD at 420 nm |
|---|---|
| 2 Nyanza gpe I | 3.029 |
| 3 Poona gpe I | 3.103 |
| 11 gpe II | 3.155 |
| 12 gpe II | 0.751 |
| 18 gpe IIIa | 3.139 |
| 20 gpe IIIa | 3.068 |
| 21 gpe IIIb | 3.161 |
| 30 gpe IIIb | 3.201 |
| 31 gpe IV | 0.272 |
| 35 gpe IV | 0.527 |
| 36 gpe V | 1.868 |
| 40 gpe V | 3.347 |
| 45 gpe VI | 0.900 |
| Klebsiella oxytoca | 0.022 |
| Klebsiella pneumoniae | 0.017 |
| Acinetobacter baumanii | 0.024 |
| Proteus mirabilis | 0.019 |
| Serratia marcescens | 0.019 |
| Enterobacter agglomerans | 0.023 |
| Mycobacterium avium n° 6 | 0.025 |
| Mycobacterium tuberculosis H 37 RV | 0.020 |
| Listeria monocytogenes 1/2 LG3 | 0.015 |
| Control water | 0.018 |
| Control water | 0.022 |

We claim:

1. A purified and/or isolated DNA sequence having a length of at most 34 nucleotides and comprising a nucleotide sequence selected from the group consisting of SEQ ID NO:4, 5, 6, 7, 8, 9, 10, 11, 12, 13, 14, 15, 16, 17, 18, 19, 28 and 29.

2. A pair of DNA sequences of claim 1, consisting of SEQ ID NO:8 and 9 or SEQ ID NO:10 and 11.

3. A labeled DNA sequence of claim 1, wherein the DNA sequence consists of SEQ ID NO:6, 7, 11, or 12.

4. A kit comprising at least one DNA sequence of claim 1.

5. A kit comprising:

(a) a pair of DNA sequences of claim 2

(b) an oligonucleotide consisting of SEQ ID NO:6; and (c) an oligonucleotide consisting of SEQ ID NO:7.

6. A kit comprising an oligonucleotide consisting of SEQ ID NO:14 and an oligonucleotide consisting of SEQ ID NO:19.

7. The DNA of claim 1, wherein said DNA specifically detects *Salmonella enterica* group I.

8. The DNA sequence of claim 1, wherein the DNA sequence consists of SEQ ID NO:4, 5, 6, 7, 8, 9, 10, 11, 12, 13, 14, 15, 16, 17, 18, 19, 28, and 29.

9. A purified and/or isolated DNA sequence having a length of at most 34 nucleotides which hybridizes under stringent conditions with the DNA of claim 1 wherein stringent hybridization conditions are 10×Denharts, 6×SSC, 0.1% SDS at 42° C., followed by washing at 0.1×SSC and 0.1% SDS at 42° C.

* * * * *

UNITED STATES PATENT AND TRADEMARK OFFICE
CERTIFICATE OF CORRECTION

PATENT NO. : 5,824,795

DATED : October 20, 1998

INVENTOR(S): Michel Y. POPOFF et al.

It is certified that an error appears in the above-identified patent and that said Letters Patent is hereby corrected as shown below:

Column 39, line 32, "SEQ ID NO:6, 7, 11, or 12." should read --SEQ ID NO: 6, 7, 12 or 13.--.

Signed and Sealed this

Tenth Day of April, 2001

Attest:

NICHOLAS P. GODICI

Attesting Officer     Acting Director of the United States Patent and Trademark Office

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 2406 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
    ( A ) ORGANISM: SALMONELLA SER. TYPHI ( i x ) FEATURE:
    ( A ) NAME/KEY: CDS
    ( B ) LOCATION: 97..1755
    ( D ) OTHER INFORMATION: /product="iagA"

( i x ) FEATURE:
    ( A ) NAME/KEY: CDS
    ( B ) LOCATION: 1776..2255
    ( D ) OTHER INFORMATION: /product="iagB"

( x i ) SEQUENCE DESCRIPTION: SEQ ID NO:1:

```
GTACTAGCAG CAGAATTACT GAAACAGTAG ATTCTATCCT AACGACTTGT ATTAGCTATT                    60

ATAACTTTTC ACCCTGTAAG AGAATACACT ATTATC ATG CCA CAT TTT AAT CCT                     114
                                        Met Pro His Phe Asn Pro
                                         1               5

GTT CCT GTA TCG AAT AAA AAA TTC GTC TTT GAT GAT TTC ATA CTC AAC                     162
Val Pro Val Ser Asn Lys Lys Phe Val Phe Asp Asp Phe Ile Leu Asn
            10              15                  20

ATG GAC GGC TCC CTC GTA CGC TCA GAA AAG AAA GTC AAT ATT CCG CCA                     210
Met Asp Gly Ser Leu Val Arg Ser Glu Lys Lys Val Asn Ile Pro Pro
        25              30                  35

AAA GAA TAT GCC GTT CTG GTC ATC CTG CTC GAA GCC GCC GGC AAG ATT                     258
Lys Glu Tyr Ala Val Leu Val Ile Leu Leu Glu Ala Ala Gly Lys Ile
    40                  45                  50

GTG AGT AAA AAC ACC TTA TTG GAC CAA GTA TGG GGC GAC GCG GAA GTT                     306
Val Ser Lys Asn Thr Leu Leu Asp Gln Val Trp Gly Asp Ala Glu Val
55              60                  65                      70

AAC GAA GAA TCT CTT ACC CGC TGT ATC TAT GCC TTA CGA CGT ATT CTG                     354
Asn Glu Glu Ser Leu Thr Arg Cys Ile Tyr Ala Leu Arg Arg Ile Leu
                75                  80                  85

TCG GAA GAT AAA GAG CAT CGT TAC ATT GAA ACA CTG TAC GGA CAG GGT                     402
Ser Glu Asp Lys Glu His Arg Tyr Ile Glu Thr Leu Tyr Gly Gln Gly
            90              95                  100

TAT CGG TTT AAT CGT CCG GTC GTA GTG GTG TCT CCG CCA GCG CCG CAA                     450
Tyr Arg Phe Asn Arg Pro Val Val Val Val Ser Pro Pro Ala Pro Gln
        105             110                 115

CCT ACG ACT CAT ACA TTG GCG ATA CTT CCT TTT CAG ATG CAG GAT CAG                     498
Pro Thr Thr His Thr Leu Ala Ile Leu Pro Phe Gln Met Gln Asp Gln
    120                 125                 130

GTT CAA TCC GAG AGT CTG CAT TAC TCT ATC GTG AAG GGA TTA TCG CAG                     546
Val Gln Ser Glu Ser Leu His Tyr Ser Ile Val Lys Gly Leu Ser Gln
135             140                 145                     150

TAT GCG CCC TTT GGC CTG AGC GTG CTG CCG GTG ACC ATT ACG AAG AAC                     594
Tyr Ala Pro Phe Gly Leu Ser Val Leu Pro Val Thr Ile Thr Lys Asn
                155                 160                 165

TGC CGC AGT GTT AAG GAT ATT CTT GAG CTC ATG GAT CAA TTA CGC CCC                     642
Cys Arg Ser Val Lys Asp Ile Leu Glu Leu Met Asp Gln Leu Arg Pro
            170                 175                 180

GAT TAT TAT ATC TCC GGG CAG ATG ATA CCC GAT GGT AAT GAT AAT ATT                     690
Asp Tyr Tyr Ile Ser Gly Gln Met Ile Pro Asp Gly Asn Asp Asn Ile
        185                 190                 195

GTA CAG ATC GAG ATA GTT CGG GTT AAA GGT TAT CAC CTG CTG CAC CAG                     738
Val Gln Ile Glu Ile Val Arg Val Lys Gly Tyr His Leu Leu His Gln
    200                 205                 210

GAA AGC ATT AAG TTG ATA GAA CAC CAA CCC GCT TCT CTC TTG CAA AAC                     786
Glu Ser Ile Lys Leu Ile Glu His Gln Pro Ala Ser Leu Leu Gln Asn
215                 220                 225                 230
```

| | | | | | | | | | | | | | | | | |
|---|---|---|---|---|---|---|---|---|---|---|---|---|---|---|---|---|
| AAA | ATT | GCG | AAT | CTT | TTG | CTC | AGA | TGT | ATT | CCC | GGA | CTT | CGC | TGG | GAC | 834 |
| Lys | Ile | Ala | Asn | Leu | Leu | Leu | Arg | Cys | Ile | Pro | Gly | Leu | Arg | Trp | Asp | |
| | | | 235 | | | | | 240 | | | | | 245 | | | |
| ACA | AAG | CAA | ATT | AGC | GAG | CTA | AAT | TCG | ATT | GAC | AGT | ACC | ATG | GTC | TAC | 882 |
| Thr | Lys | Gln | Ile | Ser | Glu | Leu | Asn | Ser | Ile | Asp | Ser | Thr | Met | Val | Tyr | |
| | | | 250 | | | | 255 | | | | | 260 | | | | |
| TTA | CGC | GGT | AAG | CAT | GAG | TTA | AAT | CAA | TAC | ACC | CCC | TAT | AGC | TTA | CAG | 930 |
| Leu | Arg | Gly | Lys | His | Glu | Leu | Asn | Gln | Tyr | Thr | Pro | Tyr | Ser | Leu | Gln | |
| | | 265 | | | | | 270 | | | | | 275 | | | | |
| CAA | GCG | CTT | AAA | TTG | CTG | ACT | CAA | TGC | GTT | AAT | ATG | TCG | CCA | AAC | AGC | 978 |
| Gln | Ala | Leu | Lys | Leu | Leu | Thr | Gln | Cys | Val | Asn | Met | Ser | Pro | Asn | Ser | |
| | 280 | | | | | 285 | | | | | 290 | | | | | |
| ATT | GCG | CCT | TAC | TGT | GCG | CTG | GCA | GAA | TGC | TAC | CTC | AGC | ATG | GCG | CAA | 1026 |
| Ile | Ala | Pro | Tyr | Cys | Ala | Leu | Ala | Glu | Cys | Tyr | Leu | Ser | Met | Ala | Gln | |
| 295 | | | | 300 | | | | | 305 | | | | | 310 | | |
| ATG | GGG | ATT | TTT | GAT | AAA | CAA | AAC | GCA | ATG | ATC | AAA | GCT | AAA | GAA | CAT | 1074 |
| Met | Gly | Ile | Phe | Asp | Lys | Gln | Asn | Ala | Met | Ile | Lys | Ala | Lys | Glu | His | |
| | | | | 315 | | | | 320 | | | | | 325 | | | |
| GCT | ATT | AAG | GCG | ACA | GAG | CTG | GAC | CAC | AAT | AAT | CCA | CAA | GCT | TTA | GGA | 1122 |
| Ala | Ile | Lys | Ala | Thr | Glu | Leu | Asp | His | Asn | Asn | Pro | Gln | Ala | Leu | Gly | |
| | | | 330 | | | | | 335 | | | | | 340 | | | |
| TTA | CTG | GGG | CTA | ATT | AAT | ACG | ATT | CAC | TCA | GAA | TAC | ATC | GTC | GGG | AGT | 1170 |
| Leu | Leu | Gly | Leu | Ile | Asn | Thr | Ile | His | Ser | Glu | Tyr | Ile | Val | Gly | Ser | |
| | | 345 | | | | | 350 | | | | | 355 | | | | |
| TTA | CTA | TTC | AAA | CAA | GCT | AAC | TTA | CTT | TCG | CCC | ATT | TCT | GCA | GAT | ATT | 1218 |
| Leu | Leu | Phe | Lys | Gln | Ala | Asn | Leu | Leu | Ser | Pro | Ile | Ser | Ala | Asp | Ile | |
| | 360 | | | | | 365 | | | | | 370 | | | | | |
| AAA | TAT | TAT | TAT | GGC | TGG | AAT | CTT | TTC | ATG | GCT | GGT | CAG | TTG | GAG | GAG | 1266 |
| Lys | Tyr | Tyr | Tyr | Gly | Trp | Asn | Leu | Phe | Met | Ala | Gly | Gln | Leu | Glu | Glu | |
| 375 | | | | 380 | | | | | 385 | | | | | 390 | | |
| GCC | TTA | CAA | ACG | ATT | AAC | GAG | TGT | TTA | AAA | TTG | GAC | CCA | ACG | CGC | GCA | 1314 |
| Ala | Leu | Gln | Thr | Ile | Asn | Glu | Cys | Leu | Lys | Leu | Asp | Pro | Thr | Arg | Ala | |
| | | | | 395 | | | | 400 | | | | | 405 | | | |
| GCC | GCA | GGG | ATC | ACT | AAG | CTG | TGG | ATT | ACC | TAT | TAT | CAT | ACC | GGT | ATT | 1362 |
| Ala | Ala | Gly | Ile | Thr | Lys | Leu | Trp | Ile | Thr | Tyr | Tyr | His | Thr | Gly | Ile | |
| | | | 410 | | | | 415 | | | | | 420 | | | | |
| GAT | GAT | GCT | ATA | CGT | TTA | GGC | GAT | GAA | TTA | CGC | TCA | CAA | CAC | CTG | CAG | 1410 |
| Asp | Asp | Ala | Ile | Arg | Leu | Gly | Asp | Glu | Leu | Arg | Ser | Gln | His | Leu | Gln | |
| | | 425 | | | | | 430 | | | | | 435 | | | | |
| GAT | AAT | CCA | ATA | TTA | TTA | AGT | ATG | CAG | GTT | ATG | TTT | CTT | TCG | CTT | AAA | 1458 |
| Asp | Asn | Pro | Ile | Leu | Leu | Ser | Met | Gln | Val | Met | Phe | Leu | Ser | Leu | Lys | |
| | 440 | | | | | 445 | | | | | 450 | | | | | |
| GGT | AAA | CAT | GAA | CTG | GCA | CGA | AAA | TTA | ACT | AAA | GAA | ATA | TCC | ACG | CAG | 1506 |
| Gly | Lys | His | Glu | Leu | Ala | Arg | Lys | Leu | Thr | Lys | Glu | Ile | Ser | Thr | Gln | |
| 455 | | | | 460 | | | | | 465 | | | | | 470 | | |
| GAA | ATA | ACA | GGA | CTT | ATT | GCT | GTT | AAT | CTT | CTT | TAC | GCT | GAA | TAT | TGT | 1554 |
| Glu | Ile | Thr | Gly | Leu | Ile | Ala | Val | Asn | Leu | Leu | Tyr | Ala | Glu | Tyr | Cys | |
| | | | | 475 | | | | 480 | | | | | 485 | | | |
| CAG | AAT | AGT | GAG | CGT | GCC | TTA | CCG | ACG | ATA | AGA | GAA | TTT | CTG | GAA | AGT | 1602 |
| Gln | Asn | Ser | Glu | Arg | Ala | Leu | Pro | Thr | Ile | Arg | Glu | Phe | Leu | Glu | Ser | |
| | | | 490 | | | | | 495 | | | | | 500 | | | |
| GAA | CAG | CGT | ATA | GAT | AAT | AAT | CCG | GGA | TTA | TTA | CCG | TTA | GTG | CTG | GTT | 1650 |
| Glu | Gln | Arg | Ile | Asp | Asn | Asn | Pro | Gly | Leu | Leu | Pro | Leu | Val | Leu | Val | |
| | | 505 | | | | | 510 | | | | | 515 | | | | |
| GCC | CAC | GGC | GAA | GCT | ATT | GCC | GAG | AAA | ATG | TGG | AAT | AAA | TTT | AAA | AAC | 1698 |
| Ala | His | Gly | Glu | Ala | Ile | Ala | Glu | Lys | Met | Trp | Asn | Lys | Phe | Lys | Asn | |
| | 520 | | | | | 525 | | | | | 530 | | | | | |
| GAA | GAC | AAT | ATT | TGG | TTC | AAA | AGA | TGG | AAA | CAG | GAT | CCC | CGC | TTG | ATT | 1746 |
| Glu | Asp | Asn | Ile | Trp | Phe | Lys | Arg | Trp | Lys | Gln | Asp | Pro | Arg | Leu | Ile | |
| 535 | | | | 540 | | | | | 545 | | | | | 550 | | |

```
AAA TTA CGG TAAAATCTGA GAGAGGAGAT ATG CAT TAT TTT TTT ATC ATC       1796
Lys Leu Arg                         Met His Tyr Phe Phe Ile Ile
                                     1               5

GTA ATC TGG TTG CTT AGC ATA AAT ACG GCA TGG GCT GAT TGC TGG CTT     1844
Val Ile Trp Leu Leu Ser Ile Asn Thr Ala Trp Ala Asp Cys Trp Leu
         10              15                      20

CAG GCT GAA AAA ATG TTC AAT ATT GAA TCC GAA CTA CTT TAC GCT ATC     1892
Gln Ala Glu Lys Met Phe Asn Ile Glu Ser Glu Leu Leu Tyr Ala Ile
     25              30                      35

GCC CAG CAG GAA TCG GCG ATG AAA CCT GGC GCC ATT GGT CAT AAC CGA     1940
Ala Gln Gln Glu Ser Ala Met Lys Pro Gly Ala Ile Gly His Asn Arg
 40              45                  50                      55

GAT GGT TCA ACC GAT CTT GGC CTG ATG CAA ATT AAC AGC TTC CAT ATG     1988
Asp Gly Ser Thr Asp Leu Gly Leu Met Gln Ile Asn Ser Phe His Met
             60              65                      70

AAA AGG CTG AAA AAA ATG GGG ATT AGT GAA AAA CAG TTG TTA CAG GAT     2036
Lys Arg Leu Lys Lys Met Gly Ile Ser Glu Lys Gln Leu Leu Gln Asp
             75              80                      85

CCC TCG ATT TCT GTC ATT GTG GGC GCA TCC ATT TTA TCA GAT ATG ATG     2084
Pro Ser Ile Ser Val Ile Val Gly Ala Ser Ile Leu Ser Asp Met Met
             90              95                     100

AAA ATC TAC GGT TTT AGC TGG GAG GCC GTT GGC GCT TAT AAT GCC GGG     2132
Lys Ile Tyr Gly Phe Ser Trp Glu Ala Val Gly Ala Tyr Asn Ala Gly
105             110                     115

ACG TCG CCG AAA CGA TCG GAT ATA AGG AAA CGT TAT GCT AAA AAA ATT     2180
Thr Ser Pro Lys Arg Ser Asp Ile Arg Lys Arg Tyr Ala Lys Lys Ile
120             125                     130                    135

TGG GAG AAT TAC AGA AAA TTA AAA GAG ATG TCA GCA GAA GAG AAA AAC     2228
Trp Glu Asn Tyr Arg Lys Leu Lys Glu Met Ser Ala Glu Glu Lys Asn
                140             145                     150

AAA AGA CTT TCT ATC GCG GTA AAC AAA TAATTATACA GGAATAGCTT           2275
Lys Arg Leu Ser Ile Ala Val Asn Lys
                155             160

ACTTTCAGAT AATTCTAAAA GTAAGCTATG TTTTTATCAG CTTGCCGTCG TCATAAGCAA   2335

CTGGCGCTTG CATTGCTTTT AGTTGTACAA ACTGTGAGGC GTCTTCCAGC ATTCTATTGT   2395

TCCGTGAATT C                                                       2406
```

( 2 ) INFORMATION FOR SEQ ID NO:2:

( i ) SEQUENCE CHARACTERISTICS:
        ( A ) LENGTH: 553 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro His Phe Asn Pro Val Pro Val Ser Asn Lys Lys Phe Val Phe
 1               5                  10                      15

Asp Asp Phe Ile Leu Asn Met Asp Gly Ser Leu Val Arg Ser Glu Lys
             20              25                      30

Lys Val Asn Ile Pro Pro Lys Glu Tyr Ala Val Leu Val Ile Leu Leu
             35              40                      45

Glu Ala Ala Gly Lys Ile Val Ser Lys Asn Thr Leu Leu Asp Gln Val
 50              55                      60

Trp Gly Asp Ala Glu Val Asn Glu Glu Ser Leu Thr Arg Cys Ile Tyr
65               70                      75                   80

Ala Leu Arg Arg Ile Leu Ser Glu Asp Lys Glu His Arg Tyr Ile Glu
             85                      90                      95
```

-continued

| | | | | | | | | | | | | | | |
|---|---|---|---|---|---|---|---|---|---|---|---|---|---|---|
| Thr | Leu | Tyr | Gly<br>100 | Gln | Gly | Tyr | Arg<br>105 | Phe | Asn | Arg | Pro | Val<br>110 | Val | Val |
| Ser | Pro | Pro<br>115 | Ala | Pro | Gln | Pro<br>120 | Thr | Thr | His | Thr | Leu<br>125 | Ala | Ile | Leu | Pro |
| Phe<br>130 | Gln | Met | Gln | Asp | Gln<br>135 | Val | Gln | Ser | Glu | Ser<br>140 | Leu | His | Tyr | Ser | Ile |
| Val<br>145 | Lys | Gly | Leu | Ser | Gln<br>150 | Tyr | Ala | Pro | Phe | Gly<br>155 | Leu | Ser | Val | Leu | Pro<br>160 |
| Val | Thr | Ile | Thr | Lys<br>165 | Asn | Cys | Arg | Ser | Val<br>170 | Lys | Asp | Ile | Leu | Glu<br>175 | Leu |
| Met | Asp | Gln | Leu<br>180 | Arg | Pro | Asp | Tyr | Tyr<br>185 | Ile | Ser | Gly | Gln | Met<br>190 | Ile | Pro |
| Asp | Gly | Asn<br>195 | Asp | Asn | Ile | Val | Gln<br>200 | Ile | Glu | Ile | Val | Arg<br>205 | Val | Lys | Gly |
| Tyr | His<br>210 | Leu | Leu | His | Gln | Glu<br>215 | Ser | Ile | Lys | Leu | Ile<br>220 | Glu | His | Gln | Pro |
| Ala<br>225 | Ser | Leu | Leu | Gln | Asn<br>230 | Lys | Ile | Ala | Asn | Leu<br>235 | Leu | Leu | Arg | Cys | Ile<br>240 |
| Pro | Gly | Leu | Arg | Trp<br>245 | Asp | Thr | Lys | Gln | Ile<br>250 | Ser | Glu | Leu | Asn | Ser<br>255 | Ile |
| Asp | Ser | Thr | Met<br>260 | Val | Tyr | Leu | Arg | Gly<br>265 | Lys | His | Glu | Leu | Asn<br>270 | Gln | Tyr |
| Thr | Pro | Tyr<br>275 | Ser | Leu | Gln | Gln | Ala<br>280 | Leu | Lys | Leu | Leu | Thr<br>285 | Gln | Cys | Val |
| Asn | Met<br>290 | Ser | Pro | Asn | Ser | Ile<br>295 | Ala | Pro | Tyr | Cys | Ala<br>300 | Leu | Ala | Glu | Cys |
| Tyr<br>305 | Leu | Ser | Met | Ala | Gln<br>310 | Met | Gly | Ile | Phe | Asp<br>315 | Lys | Gln | Asn | Ala | Met<br>320 |
| Ile | Lys | Ala | Lys | Glu<br>325 | His | Ala | Ile | Lys | Ala<br>330 | Thr | Glu | Leu | Asp | His<br>335 | Asn |
| Asn | Pro | Gln | Ala<br>340 | Leu | Gly | Leu | Leu | Gly<br>345 | Leu | Ile | Asn | Thr | Ile<br>350 | His | Ser |
| Glu | Tyr | Ile<br>355 | Val | Gly | Ser | Leu | Leu<br>360 | Phe | Lys | Gln | Ala | Asn<br>365 | Leu | Leu | Ser |
| Pro | Ile<br>370 | Ser | Ala | Asp | Ile | Lys<br>375 | Tyr | Tyr | Tyr | Gly | Trp<br>380 | Asn | Leu | Phe | Met |
| Ala<br>385 | Gly | Gln | Leu | Glu | Glu<br>390 | Ala | Leu | Gln | Thr | Ile<br>395 | Asn | Glu | Cys | Leu | Lys<br>400 |
| Leu | Asp | Pro | Thr | Arg<br>405 | Ala | Ala | Ala | Gly | Ile<br>410 | Thr | Lys | Leu | Trp | Ile<br>415 | Thr |
| Tyr | Tyr | His | Thr<br>420 | Gly | Ile | Asp | Asp | Ala<br>425 | Ile | Arg | Leu | Gly | Asp<br>430 | Glu | Leu |
| Arg | Ser | Gln | His<br>435 | Leu | Gln | Asp | Asn | Pro<br>440 | Ile | Leu | Leu | Ser | Met<br>445 | Gln | Val |
| Met | Phe<br>450 | Leu | Ser | Leu | Lys | Gly<br>455 | Lys | His | Glu | Leu | Ala<br>460 | Arg | Lys | Leu | Thr |
| Lys<br>465 | Glu | Ile | Ser | Thr | Gln<br>470 | Glu | Ile | Thr | Gly | Leu<br>475 | Ile | Ala | Val | Asn | Leu<br>480 |
| Leu | Tyr | Ala | Glu | Tyr<br>485 | Cys | Gln | Asn | Ser | Glu<br>490 | Arg | Ala | Leu | Pro | Thr<br>495 | Ile |
| Arg | Glu | Phe | Leu | Glu<br>500 | Ser | Glu | Gln | Arg<br>505 | Ile | Asp | Asn | Asn | Pro<br>510 | Gly | Leu |
| Leu | Pro | Leu | Val<br>515 | Leu | Val | Ala | His | Gly<br>520 | Glu | Ala | Ile | Ala<br>525 | Glu | Lys | Met |

```
Trp Asn Lys Phe Lys Asn Glu Asp Asn Ile Trp Phe Lys Arg Trp Lys
    530             535             540
Gln Asp Pro Arg Leu Ile Lys Leu Arg
545             550
```

(2) INFORMATION FOR SEQ ID NO:3:

(i) SEQUENCE CHARACTERISTICS:
        (A) LENGTH: 160 amino acids
        (B) TYPE: amino acid
        (D) TOPOLOGY: linear (ii) MOLECULE TYPE: protein (xi) SEQUENCE DESCRIPTION: SEQ ID NO:3:

```
Met His Tyr Phe Phe Ile Ile Val Ile Trp Leu Leu Ser Ile Asn Thr
 1               5                  10                  15
Ala Trp Ala Asp Cys Trp Leu Gln Ala Glu Lys Met Phe Asn Ile Glu
            20                  25                  30
Ser Glu Leu Leu Tyr Ala Ile Ala Gln Gln Glu Ser Ala Met Lys Pro
        35                  40                  45
Gly Ala Ile Gly His Asn Arg Asp Gly Ser Thr Asp Leu Gly Leu Met
    50                  55                  60
Gln Ile Asn Ser Phe His Met Lys Arg Leu Lys Lys Met Gly Ile Ser
65                  70                  75                  80
Glu Lys Gln Leu Leu Gln Asp Pro Ser Ile Ser Val Ile Val Gly Ala
                85                  90                  95
Ser Ile Leu Ser Asp Met Met Lys Ile Tyr Gly Phe Ser Trp Glu Ala
            100                 105                 110
Val Gly Ala Tyr Asn Ala Gly Thr Ser Pro Lys Arg Ser Asp Ile Arg
        115                 120                 125
Lys Arg Tyr Ala Lys Lys Ile Trp Glu Asn Tyr Arg Lys Leu Lys Glu
    130                 135                 140
Met Ser Ala Glu Glu Lys Asn Lys Arg Leu Ser Ile Ala Val Asn Lys
145                 150                 155                 160
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

TATTAAGTAT GCAGGTTATG        20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

AGAGAATTTC TGCAAAGTGA A        21

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

ATATCCACGC AGGAAATAAC AGGACTT　　　　　　　　　　　　　　　　27

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

GAGCGTGCCT TACCGACGAT A　　　　　　　　　　　　　　　　　21

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

GCAGGGATCA CTAAGCTGTG　　　　　　　　　　　　　　　　　　20

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

CGTGGGCAAC CAGCACTAAC G　　　　　　　　　　　　　　　　　21

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

CGGGTTAAAG GTTATCACCT　　　　　　　　　　　　　　　　　　20

( 2 ) INFORMATION FOR SEQ ID NO:11:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (i i) MOLECULE TYPE: other nucleic acid (x i) SEQUENCE DESCRIPTION: SEQ ID NO:11:

AGCATGGCGC AAATGGG 17

(2) INFORMATION FOR SEQ ID NO:12:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (i i) MOLECULE TYPE: other nucleic acid (x i) SEQUENCE DESCRIPTION: SEQ ID NO:12:

GCACCAGGAA AGCATTAAGT TGATAGAACA C 31

(2) INFORMATION FOR SEQ ID NO:13:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (i i) MOLECULE TYPE: other nucleic acid (x i) SEQUENCE DESCRIPTION: SEQ ID NO:13:

CTTCGCTGGG ACACAAAGCA 20

(2) INFORMATION FOR SEQ ID NO:14:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (i i) MOLECULE TYPE: other nucleic acid (x i) SEQUENCE DESCRIPTION: SEQ ID NO:14:

TAATGCTTTC CTGGTGC 17

(2) INFORMATION FOR SEQ ID NO:15:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (i i) MOLECULE TYPE: other nucleic acid (x i) SEQUENCE DESCRIPTION: SEQ ID NO:15:

TACGGCATGG GCTGATTGCT 20

(2) INFORMATION FOR SEQ ID NO:16:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (i i) MOLECULE TYPE: other nucleic acid ( x i ) SEQUENCE DESCRIPTION: SEQ ID NO:16:

TTACGCTATC GCCCAGCAGC AGGA                                                                          24

( 2 ) INFORMATION FOR SEQ ID NO:17:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:17:

TGGTCATAAC CGAGATGGTT CAAACGATC                                                                     29

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:18:

ACAGTTGTTA CAGGATCCCT                                                                               20

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:19:

CCGGGCAGAT GATACCC                                                                                  17

( 2 ) INFORMATION FOR SEQ ID NO:20:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

TATTATCATA CCGGTATTGA TGATGCTATA CGTTTAGGCG ATGAATTACG CTCACAACAC                                    60

CTGCAGGATA ATCCAATATT ATTAAGTATG CAGGTTATGT TTCTTTCGCT TAAAGGTAAA                                   120

CATGAACTGG CACGAAAATT AACTAAAGAA ATATCCACGC AGGAAATAAC AGGACTTATT                                   180

GCTGTTAATC TTCTTTACGC TGAATATTGT CAGAATAGTG AGCGTGCCTT ACCGACGATA                                   240

AGAGAATTTC TGGAAAGTGA ACAGCGTATA GATAATAATC CGGGATTATT ACCGTTAGTG                                   300

( 2 ) INFORMATION FOR SEQ ID NO:21:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

| TATTATCATA | CTGGTATTGA | TGATGCTATA | CGTTTAGGCG | ATGAATTACG | CTCACAACAC | 60 |
| TGCAGGATA | ATCCAATATT | ATTAAGTATG | CAGGTTATGT | TTCTTTCTCT | TAAAGGTAAA | 120 |
| CATGAACTGG | CACGAAAATT | ATCTAAAGAA | ATATCCACGC | AGGAAATAAC | AGGGCTTATT | 180 |
| GCTGTTAATC | TTCTTTATGC | TGAATACTGT | CAGAATAGTG | AGCGTGCCTT | ACCGACGATA | 240 |
| AGAGAATTTC | TGGAAAGTGA | ACAGCGTATA | GATAATAATC | CGGGATTATT | ACCGTTAGTG | 300 |

( 2 ) INFORMATION FOR SEQ ID NO:22:

( i ) SEQUENCE CHARACTERISTICS:
( A ) LENGTH: 300 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:22:

| TATTATCATA | CCGGCATTGA | TGATGCCATA | CGTTTAGGAG | ATGAACTACG | CTCACAGCAC | 60 |
| CTGCAGGATA | ATCCCATTTT | ATTAAGTATG | CAGGTTATGT | TTCTTTCGCT | TAAAGGTAAA | 120 |
| CATGAGCTGG | CACGAAAATT | AACTAAAGAG | ACATCCCCGC | ATGAGATAAC | AGGGCTTATT | 180 |
| GCTATTAATC | TTCTTTATGC | TGAATACTGT | CAGAATAGTG | AGCGAGCCTT | ACCGAGGATA | 240 |
| AGAGAATATC | TGGCAAGTGA | ACGGAGTATT | GATAATAATC | CTGGACTATT | ACCGTTAGTG | 300 |

( 2 ) INFORMATION FOR SEQ ID NO:23:

( i ) SEQUENCE CHARACTERISTICS:
( A ) LENGTH: 300 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:23:

| TATTATCATG | CCGGCATTGA | TGATGCTATA | CGTTTAGGAG | ATGAATTACG | TTCACAACAT | 60 |
| CTGCAGGATA | ATCCAATACT | ATTAAGTATG | CAGGTTATGT | TTCTTTCGCT | TAAAGGTAAA | 120 |
| CATGAACTGG | CACGAAAATT | AGCTAAAGAA | ATATCCAAGC | ATGAAATAAC | AGGGCTTATT | 180 |
| GCTGTTAATC | TTCTGTATGC | TGAATACTGT | CAGAATAGCG | AGCGTGCATT | ACCGAGGATA | 240 |
| AGAGAGTTTC | TGGAAAGTGA | ACAGAATACT | GATAATAATC | CCGGGCTATT | ACCGTTAGTG | 300 |

( 2 ) INFORMATION FOR SEQ ID NO:24:

( i ) SEQUENCE CHARACTERISTICS:
( A ) LENGTH: 300 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:24:

| TACTATCATA | CTGGCCTTGA | TGATGCTATA | CGTTTAGGAG | ATGAATTACG | TTCGCAACAT | 60 |
| TTGCAGGATA | ATCCAATATT | ATTAAGTATG | CAGGTTATGT | TTCTTTCGCT | TAAAGGTAAA | 120 |
| CATGAACTGG | CACGAAAATT | AACTAAAGAA | ATATCCACAC | ATGAAATAAC | AGGGCTTATT | 180 |

| GCTGTTAATC | TTCTTTATGC | TGAATACTGT | CAGAATAGTG | AGCGTGCCTT | AGCGACGATA | 240 |
| AGAGAATTTC | TGGAAAGTGA | ACAGAGTGTT | GATAATAACC | CAGGGTTATT | ACCGTTAGTG | 300 |

( 2 ) INFORMATION FOR SEQ ID NO:25:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

| TATTATCAGA | CTGGCATTGA | TGATGCTATA | CGTTTAGGCG | ATGAATTACG | CTCACAATAT | 60 |
| CTGCAAGATA | ATCCAATATT | ATTAAGTATG | CAGCTTATGT | TTCTTTCGCT | TAAAGGTAAA | 120 |
| CATGAGTTGG | CACGAAAATT | AGCTAAAGAA | ATATCCACAC | ACGAAGTAAC | AGGGCTTATT | 180 |
| GCTGTTAATC | TTCTTTATGC | TGAATACTGT | CAGAATAGCG | AGCGTGCTTT | ACCGGCGATA | 240 |
| AGAGAATTTC | TGGAAAGTGA | ACAGAATATA | GATAATAATC | CGGGGCTATT | ACCGTTAGTG | 300 |

( 2 ) INFORMATION FOR SEQ ID NO:26:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

| TACTATCATA | CAGGCCTTGA | TGATGCTATA | CGTTTAGGCG | ATGAATTACG | TACACAACAT | 60 |
| TTGCAAGATA | ATCCTATATT | ATTAAGTATG | CAAGTTATGT | TTCTTTCGCT | TAAAGGTAAA | 120 |
| CATGAACTGG | CACGGCTATT | AGCTAAAGAA | ATATCCTCAC | ATGAAATAAC | AGGGCTTATT | 180 |
| GCTATTAATC | TTCTTTATGC | TGAATATTGT | CAGAATAGTG | AGCGCGCCTT | ACCGGCGATA | 240 |
| AAAGAATTTC | TGGAAAGTGA | ACAAAATATT | GACAATAACC | CTGGGCTATT | ACCGTTAGTG | 300 |

( 2 ) INFORMATION FOR SEQ ID NO:27:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

| TATTATCATA | CCGGCATTGA | TGATGCTATA | CGGTTAGGAG | ATGAATTACG | TTCACAACAC | 60 |
| TTGCAGGATA | ATCCAATATT | ATTAAGTATG | CAGGTTATGT | TTCTTTCGCT | TAAAGGTAAA | 120 |
| CATGAACTGG | CACGAAAATT | AACTAAAGAA | ATATCCAGAC | ATGAAATAAC | AGGGCTTATT | 180 |
| GCTGTTAATC | TTCTTTATGC | TGAATACTGT | CAGAATAGTG | AGCGTGCCTT | ATCGAGGATA | 240 |
| AGAGAATTTC | TGGAAAGTGA | ACAGAGTATT | GATAATAATC | CAGGACTATT | ACCGTTAGTG | 300 |

( 2 ) INFORMATION FOR SEQ ID NO:28:

( i ) SEQUENCE CHARACTERISTICS:
        ( A ) LENGTH: 34 base pairs
        ( B ) TYPE: nucleic acid
        ( C ) STRANDEDNESS: single -continued (D) TOPOLOGY: linear (ii) MOLECULE TYPE: other nucleic acid (xi) SEQUENCE DESCRIPTION: SEQ ID NO:28:

CCCGAACTAT CTCGATCTGT ACAATATTAT CATT 34

(2) INFORMATION FOR SEQ ID NO:29:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:29:

GCAGGTGATT ACCTTTAA 18